United States Patent
Sawai et al.

(10) Patent No.: US 7,501,395 B2
(45) Date of Patent: Mar. 10, 2009

(54) METHOD OF SCREENING FOR ANTIANXIETY DRUGS

(75) Inventors: Toru Sawai, Tsukuba (JP); Michiyuki Suzuki, Tsukuba (JP); Carsten Beuckmann, Tsukuba (JP); Kodo Shikata, Tsukuba (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 0 days.

(21) Appl. No.: 11/380,035

(22) Filed: Apr. 25, 2006

(65) Prior Publication Data

US 2007/0160538 A1 Jul. 12, 2007

Related U.S. Application Data

(60) Provisional application No. 60/674,957, filed on Apr. 25, 2005.

(51) Int. Cl.
*A01N 38/00* (2006.01)
*A01N 37/18* (2006.01)
*A61K 49/00* (2006.01)
*A61K 39/00* (2006.01)
*A61K 39/38* (2006.01)

(52) U.S. Cl. .............................. 514/12; 514/2; 424/9.1; 424/9.2; 424/184.1; 424/185.1; 424/198.1

(58) Field of Classification Search ...................... None
See application file for complete search history.

(56) References Cited

U.S. PATENT DOCUMENTS 7,192,950 B2 * 3/2007 Aissaoui et al. ........ 514/213.01

FOREIGN PATENT DOCUMENTS

| WO | WO-99/09024  | 2/1999  |
|----|--------------|---------|
| WO | WO-99/58533  | 11/1999 |
| WO | WO-00/47576  | 8/2000  |
| WO | WO-00/47577  | 8/2000  |
| WO | WO-00/47580  | 8/2000  |
| WO | WO-01/68609  | 9/2001  |
| WO | WO-01/96302  | 12/2001 |
| WO | WO-02/44172  | 6/2002  |
| WO | WO-02/51838  | 7/2002  |
| WO | WO-02/089800 | 11/2002 |
| WO | WO-02/090355 | 11/2002 |
| WO | WO-03/002559 | 1/2003  |
| WO | WO-03/002561 | 1/2003  |
| WO | WO-03/032991 | 4/2003  |
| WO | WO-03/037847 | 5/2003  |
| WO | WO-03/041711 | 5/2003  |
| WO | WO-03/051368 | 6/2003  |
| WO | WO-03/051873 | 6/2003  |

OTHER PUBLICATIONS

R.M. Chemelli et al., "Narcolepsy in *Orexin* Knockout Mice: Molecular Genetics of Sleep Regulation" *Cell* (Aug. 20, 1999), vol. 98, pp. 437-451.

Y. Date et al., "Orexins, Orexigenic Hypothalamic Peptides, Interact with Autonomic, Neuroendocrine and Neuroregulatory Systems," *Proc. Natl. Acad. Sci. USA* (Jan. 1999), vol. 96, pp. 748-753.

L. De Lecea et al., "The Hypocretins: Hypothalamus-Specific Peptides with Neuroexcitatory Activity," *Proc. Natl. Acad. Sci. USA* (Jan. 1998), vol. 95, pp. 322-327.

J.J. Hagan et al., "Orexin A Activates Locus Coeruleus Cell Firing and Increases Arousal in the Rat" *Proc. Natl. Acad. Sci. USA* (Sep. 1999), vol. 96, pp. 10911-10916.

T. Ida et al., "Effect of Lateral Cerebroventricular Injection of the Appetite-Stimulating Neuropeptide, Orexin and Neuropeptide Y, on the Various Behavioral Activities of Rats" *Brain Res.* (1999), vol. 821, pp. 526-529.

T. Ida et al., "Possible Involvement of Orexin in the Stress Reaction in Rats" *Biochem. Biophys. Res. Commun.* (2000), vol. 270, pp. 318-323.

T. Nambu et al., "Distribution of Orexin Neurons in the Adult Rat Brain," *Brain Res.* (1999), vol. 827, pp. 243-260.

C. Peyron et al., "Neurons Containing Hypocretin (*Orexin*) Project to Multiple Neuronal Systems" *J. Neurosci.* (Dec. 1, 1998), vol. 18, pp. 9996-10015.

T. Sakurai et al., "Orexins and Orexin Receptors: A Family of Hypothalamic Neuropeptides and G Protein-Coupled Receptors that Regulate Feeding Behavior," *Cell* (Feb. 20, 1998), vol. 92, pp. 573-585.

R.K. Singareddy et al., "Hypocretins and Anxiety:Preliminary findings in Startle Potentiated Startle" *Neuropharmacology* (2004), vol. 29, Suppl. 1, p. S209 (ACNP 2004 Annual Meeting, Abstract 78).

L. De Lecea & J.G. Sutcliffe, "*The hyppcretins/orexins*: novel hypothalamic neuropeptides involved in different physiological systems" *Cell. Mol. Life Sci.* (1999), vol. 56, pp. 473-480.

\* cited by examiner

*Primary Examiner*—Olga N Chernyshev
(74) *Attorney, Agent, or Firm*—Darby & Darby P.C.

(57) ABSTRACT

An anxiolytic drug of the invention comprises an orexin receptor antagonist, a pharmacologically acceptable salt thereof, or a solvate thereof as an active ingredient. A method for screening a compound having an anxiolytic action of the invention comprises a step of using orexin-A.

4 Claims, 4 Drawing Sheets

METHOD OF SCREENING FOR ANTIANXIETY DRUGS

This application claims the benefit of U.S. provisional application No. 60/674,957, which is incorporated herein in its entirety. All of the prior art documents, laid-open patent applications, patent gazettes and other patent publications cited herein are incorporated herein by reference.

FIELD OF THE INVENTION

The present invention relates to an anxiolytic drugs and a method for screening a compound having an anxiolytic action.

BACKGROUND OF THE INVENTION

Orexin-A and orexin-B have been identified as two orphan GPCR endogenous peptide ligands (neuropeptides) (T. Sakurai et al., Cell, vol. 92 (1998), p. 573-585). Mammal orexin-A comprises 33 amino acids and has two disulfide bonds while orexin-B comprises 28 amino acids. Neurons that produce such orexins are located in lateral hypothalamic area (LHA) and posterior hypothalamus, projecting to various areas of the brain (e.g., cerebral cortex, olfactory bulb, hippocampus, amygdala, septal region, diagonal band of Broca, bed nucleus of the stria terminals, thalamus, anterior and posterior hypothalamus, midbrain, brain stem and spinal cord) (T. Sakurai et al., Cell, vol. 92 (1998), p. 573-585; Y. Date et al., Proc. Natl. Acad. Sci. USA, vol. 96 (1999), p-748-753; L. de Lecea et al., Proc. Natl. Acad. Sci. USA, vol. 95 (1998), p-322-327; T. Nambu et al., Brain Res., vol. 827 (1999), p-243-260; C. Peyron et al., J. Neurosci., vol. 18 (1998), p-9996-10015). Projections of orexin-producing neurons to such widespread areas suggest that orexin as a neuropeptide is involved in various physiologic functions.

In mammals, two orexin receptor subtypes named orexin receptor-1 ($OX_1R$) and orexin receptor-2 ($OX_2R$) have been identified (T. Sakurai et al., Cell, vol. 92 (1998), p. 573-585). As to these subtypes, $OX_2R$ is known to have generally the same level of binding affinity to both orexin-A and orexin-B whereas $OX_1R$ is known to have 100 to 1000 times higher binding affinity to orexin-A than to orexin-B. Thus, orexin-A should particularly be important as a physiologically active substance.

Orexin-A has also been reported to be involved, for example, in the control of awakening and eating behaviors (T. Sakurai et al., Cell, vol. 92 (1998), p. 573-585; R. M. Chemelli et al., Cell, vol. 98 (1999), p-437-451; J. J. Hagan et al., Proc. Natl. Acad. Sci. USA, vol. 96 (1999), p-10911-10916). Furthermore, recent reports mention its relationship with stress. For example, intracerebroventricular administration of orexin-A to a mouse increases various stress-like behaviors such as face washing, grooming, searching and burrowing (T. Ida et al., Biochem. Biophys. Res. Commun., vol. 270 (2000), p-318-323; T. Ida et al., Brain Res., vol. 821 (1999), p-526-529). Meanwhile, in relation with these various behaviors, various $OX_1R$ antagonists have also been reported (WO 99/9024; WO 99/58533; WO 00/47577; WO 00/47580; WO 00/47576; WO 01/96302; WO 02/44172; WO 03/51368; WO 03/51873; WO 03/37847; WO 03/41711; WO 03/32991; WO 03/2561; WO 03/2559; WO 02/90355; WO 02/89800; WO 02/51838; WO 01/68609).

Today, various anxiety factors existing in social environment surrounding individuals are acknowledged as a problem. Specifically, anxiety ranges from vague anxiety to specific anxiety, for example, anxiety from overwork and stress, anxiety about domestic and international situations, anxiety over the future such as severe employment prospects, anxiety associated with depression, and anxiety associated with anesthesia and operation in the medical field. In addition, there are anxieties resulting from autonomic dysfunctions such as neurosis anxiety caused by genetic factors. Such anxiety brings an abnormal sense of tension as well as rational symptoms such as sleep disorder. Thus, in order to selectively alleviate or eliminate such anxieties and tensions, various minor tranquilizers, namely anxiolytic drugs, have been used suitably.

SUMMARY OF THE INVENTION

Problems to be solved by the present invention are to provide a novel anxiolytic drug, and further to provide a novel method for screening a compound having an anxiolytic action.

The present inventors devoted themselves to keen studies to solve the problems mentioned above. In this process, the neuropeptide "orexin" (particularly orexin-A) that appeared to be involved in various physiological functions as described above was for the first time confirmed to be involved in the rise of anxiety and tension, which suggests its anxiogenic action. Given this, the present inventors focused on an idea that an orexin receptor antagonist might exert effective antagonistic action on such anxieties. As a result, use of such compound as an active ingredient of an anxiolytic drug was found to be very useful, thereby completing the present invention. Moreover, the present inventors also found that orexin-A can be used for selecting a candidate substance that can alleviate or eliminate anxiety to screen a compound having an anxiolytic action, and have completed the present invention.

Thus, the present invention is as follows.

(1) An anxiolytic drug comprising a compound that inhibits binding between an orexin receptor and orexin-A, a pharmacologically acceptable salt thereof or a solvate thereof as an active ingredient.

(2) A method for screening a compound having an anxiolytic action, comprising using orexin-A. According to this screening method a candidate substance having, for example, an orexin receptor antagonist activity can be selected.

(3) A method for screening a compound having an anxiolytic action, comprising: administrating a candidate substance to a test animal before inducing orexin-A secretion in the test animal, or administrating a candidate substance to a test animal after or simultaneously with inducing orexin-A secretion in the test animal; and thereafter analyzing the presence of anxiety in the test animal.

(4) A method for screening a compound with an anxiolytic action, comprising administrating a candidate substance to a test animal before administrating orexin-A to the test animal, or administrating a candidate substance to a test animal after or simultaneously with administrating orexin-A to the test animal; and thereafter analyzing the presence of anxiety in the test animal.

(5) A kit for screening a compound having an anxiolytic action, comprising orexin-A.

The present invention provides a novel anxiolytic drug and further a novel method for screening a compound having an anxiolytic action.

DETAILED DESCRIPTION OF THE INVENTION

Figure 1:
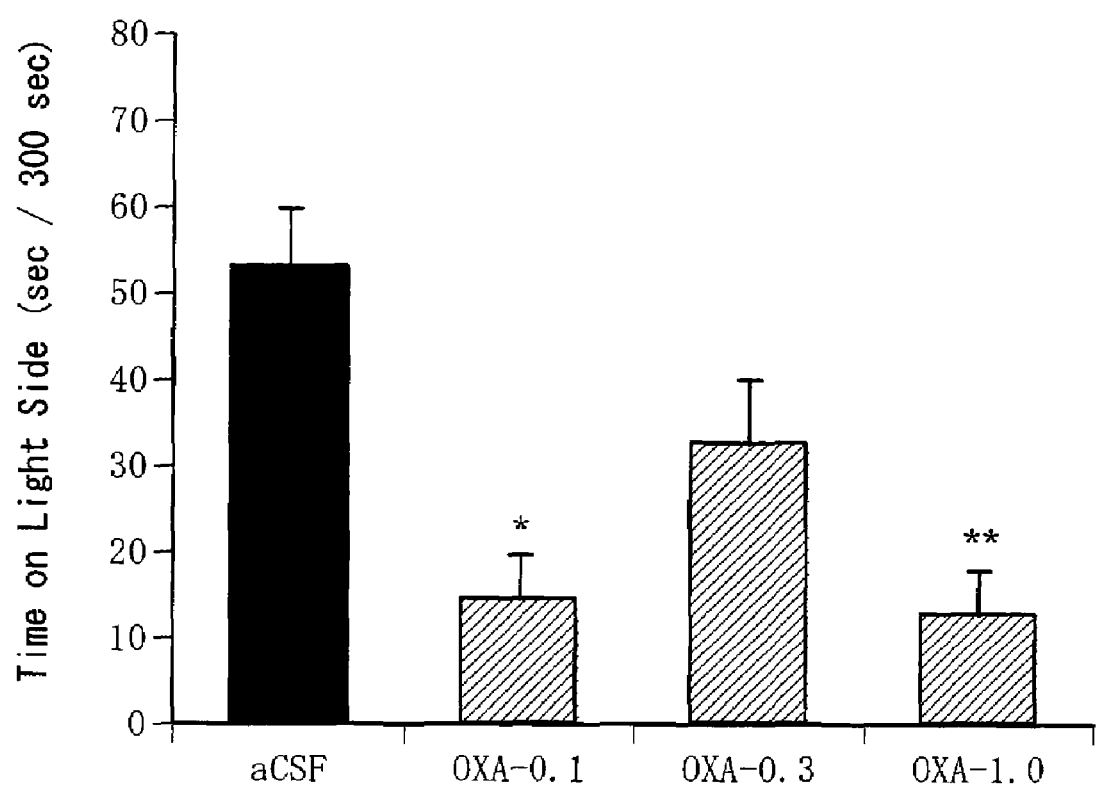
FIG. 1 shows the results from the light-dark exploration test conducted in Example 1 for confirming anxiogenic action of orexin-A.

Hereinafter, embodiments of the present invention will be described. The following embodiments are merely an illustration of the present invention and thus shall not be construed as limitation to the present invention. The present invention can be carried out in various embodiments without departing from the scope of the invention.

1. SUMMARY OF THE INVENTION

"Orexin-A" is a substance having a remarkably higher binding reactivity to orexin receptor-1 compared to another type of neuropeptide orexin-B. In view that orexin-producing neurons project to various areas of the brain, "orexin-A" is assumed to be closely related to emergence of various physiological functions. For example, its involvement in control of awakening and eating behavior, and stress or the like have already been acknowledged. However, its involvements in anxiety and tension have not been clearly recognized previously and remained no more than an assumption. Therefore, the present inventors used mice to which orexin-A was administered intracerebroventricularlly and which were examined for the presence of central action of orexin-A involved in anxiety by a light-dark exploration test and an elevated plus maze test. As a result, anxiogenic action of "orexin-A" was observed, demonstrating clearly for the first time that "orexin-A" is a physiologically active peptide that is closely related to anxiety.

The present inventors devoted themselves to keen examination based on these new findings and found the use of an orexin receptor antagonist as an active ingredient of an anxiolytic drug, which is a totally new application. In addition, they also found to use orexin-A to screen a compound with enhanced anxiolytic action by confirming a candidate substance for the presence of an antagonist action on the binding reaction described above.

2. Anxiolytic Drugs

As described above, the anxiolytic drug of the invention comprises an orexin receptor antagonist, a pharmacologically acceptable salt thereof, or a solvate thereof as an active ingredient.

The anxiolytic drug of the invention, in the same way as known anxiolytic drugs but without limitation, is mainly effective for anxiety and tension of a short duration and appropriate to any disease or condition associated with anxiety. For example, the anxiolytic drug is effective in preventing or treating diseases such as anxiety, restlessness, depression, insomnia and automatic neuropathy that appears as a leading symptom of neurosis anxiety, hypochondriasis, obsessive-compulsive neurosis, depressive neurosis, hysteria and phobia as well as conditions such as autonomic imbalance, schizophrenia, depression and alcoholic withdrawal symptoms associated with anxiety disorder and restlessness related to this disorder. Herein, the term "anxiety" is generally described as "a fear with a sense of imminent danger associated with turbulence, tension, rapid pulse, breathing difficulty or the like in a clear absence of confirmable stimulation" (Stedman's Medical Dictionary 5th Edition, published by Toshiharu Nakao, Medical View Co., Ltd., February, 2002). DSM-IV classifies "anxiety disorders" into panic disorder (300.01, 300.21), agoraphobia (300.22), phobia (300.29), social phobia (300.29), obsessive-compulsive disorder (300.3), posttraumatic stress disorder (309.81), acute stress disorder (308.3), generalized anxiety disorder, and anxiety disorder associated with general physical disorder. In ICD-10, the subcategory F4 "Neurotic, stress-related and somatoform disorders" includes, for example, agoraphobia (F40), other anxiety disorders (F41), obsessive-compulsive disorder (F42) and stress response and adjustment disorders (F43). Anxiety as used according to the present invention is defined as anxiety that does not include stress-related anxiety, for example, anxiety that does not include posttraumatic stress disorder (309.81) and acute stress disorder (308.3) in DSM-IV and/or stress response and adjustment disorders (F43) in ICD-10. Accordingly, the anxiolytic drugs of the invention should be applied to anxiety other than stress-related anxiety.

An orexin receptor antagonist is, among compounds capable of inhibiting binding reaction between orexin receptors (orexin receptor-1, orexin receptor-2) and orexin-A by having an antagonist action on such binding, a compound which does not exert a physiologic action by itself via the receptor but attenuates intensity of the signal from the orexin receptor or inhibits the signal from the orexin receptor via an antagonist action thereto. According to the present invention, orexin receptor-1 antagonist is preferable. The inhibition of the binding described above may be complete or partial inhibition of the binding reaction, including but not limited to inhibition of a binding reactivity of preferably 10% or higher, more preferably 30% or higher, more preferably 50% or higher, still more preferably 70% or higher, particularly 80% or higher, more particularly 90% or higher, and most preferably 100%.

The orexin receptor antagonist may be and not limited to one having a competitive antagonist action or one having a noncompetitive antagonist action.

The orexin receptor antagonist of the invention comprises an orexin receptor antagonist or a salt thereof that goes through in vivo metabolism such as oxidization, reduction, hydrolysis or conjugation as well as a compound that produces an orexin receptor antagonist or a salt thereof through in vivo metabolism such as oxidization, reduction or hydrolysis.

The orexin receptor antagonist comprises any isomeric form that is structurally acceptable with the compound (e.g., geometric isomer, enantiomer arising from asymmetric carbons, rotational isomer, stereoisomer and tautomer) and a mixture of two or more of these isomeric forms, and thus is not limited to structural formulae that are shown herein for the sake of convenience.

The orexin receptor antagonist may be any one of and not limited to S-form, R-form or RS-form.

The orexin receptor antagonist can be obtained by in vitro screening.

The method for screening an orexin receptor antagonist in vitro is not particularly limited, and a known screening method can be used by setting appropriate means and conditions. For example, the method preferably employs a receptor ligand (orexin-A), specific examples being methods based on binding assay, determination of second messenger concentration, determination of [$^{35}$S]-GTPγs binding activity or the like. Generally, in these screening methods, a cell capable of expressing (on the surface thereof) a receptor (orexin receptor (orexin receptor-1, orexin receptor-2)) or a membrane fraction of such cell is used. For example, such cells may be, and without limitation, animal cells (CHO cells, HEK293 cells, mouse myeloma cells, monkey COS cells, etc.), yeast, insect cells, *E. coli.* (HB101, JM103, etc.) or the like.

The binding assay mentioned above can be employed to screen an orexin receptor antagonist. For example, a membrane is prepared from a cell expressing an orexin receptor (orexin receptor-1, orexin receptor-2) (human) (e.g., a CHO cell), which is then brought into contact with a candidate substance (a candidate compound) in the presence of the receptor ligand (orexin-A) so as to analyze inhibition of functional response (e.g., binding between orexin-A and the orexin receptor), thereby screening a candidate substance with an antagonist activity. In this case, orexin-A may be, for example, radiolabeled (e.g., [$^{125}$I], [$^{3}$H], [$^{14}$C] or [$^{35}$S]), or orexin-A or the candidate substance may be fluorescently labeled. Furthermore, the binding assay may also be used for assessing antagonist action of an orexin receptor antagonist.

Without limitation, the determination of the second messenger concentration mentioned above is preferably carried out, for example, by determining the change in the intracellular calcium ion concentration. Specifically, a cell expressing an orexin receptor (orexin receptor-1, orexin receptor-2) (human) (e.g., CHO cell, HEK293 cell, etc.) and a fluorometric imaging plate reader (FLIPR; molecular Devices, UK) can be used to determine the intracellular calcium ion concentration. The procedure may comprise but without being limited to first seeding cells on a 384-well plate with black walls and a transparent bottom (e.g., at 5000 cells/well), adding Fluo-3 AM (Dojindo Laboratories) as calcium indicator to the cells, incubating the cells at 37° C. for an hour and then adding a candidate substance. Then, after incubation at the same temperature for another 30 minutes, orexin-A (e.g., 3 nM) is added and fluorescence ($\lambda_{EX}$=488 nm, $\lambda_{EM}$=540 nm) is determined with FLIPR. The measured fluorescence is compared to that where the candidate substance is not added, thereby assessing antagonist activity of the candidate substance.

Specific examples of the orexin receptor-1 antagonist include but not limited to compounds of the following formulae (1) to (14).

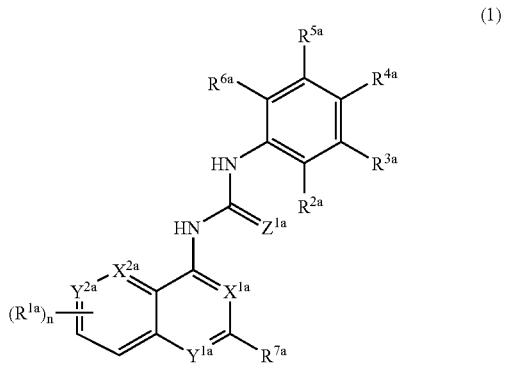

(1)

In formula (1), $R^{1a}$ is a $C_1$-$C_6$ alkyl group, a $C_2$-$C_6$ alkenyl group or a $C_1$-$C_6$ alkoxy group (each of which may be optionally substituted with a halogen atom, $R^{8a}$CO— or $NR^{9a}R^{10a}$CO—), $R^{2a}$, $R^{3a}$, $R^{4a}$, $R^{5a}$ and $R^{6a}$ is each independently a $C_1$-$C_6$ alkyl group, a $C_2$-$C_6$ alkenyl group, a $C_1$-$C_6$ alkoxy group or a $C_1$-$C_6$ alkylthio group (each of which may be optionally substituted with a hydrogen atom, a halogen atom, a nitro group, a cyano group, an aryloxy group, an aryl ($C_1$-$C_6$) alkyloxy group, an aryl ($C_1$-$C_6$)alkyl group, $R^{8a}$CO—, $R^{8a}$SO$_2$NH—, $R^{8a}$SO$_2$O—, $R^{8a}$CON($R^{11a}$)—, $NR^{9a}R^{10a}$—, $NR^{9a}R^{10a}$CO—, —COOR$^{9a}$, $R^{11a}$C(=NOR$^{8a}$), a heterocyclic group or a heterocyclic ($C_1$-$C_6$)alkyl group), or two of the adjacent $R^{2a}$, $R^{3a}$, $R^{4a}$, $R^{5a}$ and $R^{6a}$ share a carbon atom to form a carbon ring or a heterocycle (these carbon ring and heterocycle may be optionally substituted), $R^{7a}$ is a hydrogen atom, a $C_1$-$C_6$ alkyl group, a $C_2$-$C_6$ alkenyl group, a $C_1$-$C_6$ alkoxy group or a $C_1$-$C_6$ alkylthio group (each of which may be optionally substituted with a halogen atom, a hydroxyl group, a nitro group, a cyano group, $NR^{9a}R^{10a}$—, $NR^{9a}R^{10a}$CO—, $N_3$, —OCOR$^{9a}$ or $R^{8a}$CON($R^{11a}$)—), $R^{8a}$ is a $C_1$-$C_6$ alkyl group, a $C_2$-$C_6$ alkenyl group, a heterocyclic group, a heterocyclic ($C_1$-$C_6$)alkyl group, a heterocyclic ($C_2$-$C_6$)alkenyl group, an aryl group, an aryl ($C_1$-$C_6$) alkyl group or an aryl ($C_2$-$C_6$)alkenyl group (each of which may be optionally substituted), $R^{9a}$ and $R^{10a}$ are each independently a hydrogen atom, a $C_1$-$C_6$ alkyl group, a $C_2$-$C_6$ alkenyl group, a heterocyclic group, a heterocyclic ($C_1$-$C_6$)alkyl group, an aryl group or an aryl ($C_1$-$C_6$)alkyl group (each of which may be optionally substituted), $R^{11a}$ is a hydrogen atom or a $C_1$-$C_6$ alkyl group which may be optionally substituted, $X^{1a}$ and $Y^{1a}$ are each independently CH or a nitrogen atom (other than where $X^{1a}$ and $Y^{1a}$ are both CH), $X^{2a}$ and $Y^{2a}$ are each independently CH or a nitrogen atom (other than where $X^{2a}$ and $Y^{2a}$ are both nitrogen atoms), Z is an oxygen atom or a sulfur atom, n is 0, 1, 2, 3 or 4 when $X^{2a}$ and $Y^{2a}$ are both CH while 0, 1, 2 or 3 when one of $X^{2a}$ and $Y^{2a}$ is CH and the other is a nitrogen atom.

The compound represented by formula (1) can be obtained by but not limited to the process described in WO 99/09024, WO 99/58533, WO 00/47577 or WO 00/47580, or a process pursuant thereto. Specifically, the following embodiments (1-1) to (1-4) are illustrated as preferable embodiments for formula (1).

(1-1)

In one embodiment, $R^{1a}$ is a $C_1$-$C_6$ alkyl group, a $C_2$-$C_6$ alkenyl group or a $C_1$-$C_6$ alkoxy group (each of which may be optionally substituted with a halogen atom, $R^{8a}$CO— or $NR^{9a}R^{10a}$CO—), $R^{2a}$, $R^{3a}$, $R^{4a}$, $R^{5a}$ and $R^{6a}$ are each independently a $C_1$-$C_6$ alkyl group, a $C_2$-$C_6$ alkenyl group, a $C_1$-$C_6$ alkoxy group or a $C_1$-$C_6$ alkylthio group (each of which may be optionally substituted with a hydrogen atom, a halogen atom, a nitro group, a cyano group, an aryloxy group, an aryl ($C_1$-$C_6$) alkyloxy group, an aryl ($C_1$-$C_6$)alkyl group, $R^{8a}$CO—, $R^{8a}$SO$_2$NH—, $R^{8a}$CON($R^{11a}$)—, $NR^{9a}R^{10a}$—, $NR^{9a}R^{10a}$CO—, —COOR$^{9a}$ or a heterocyclic group but at least one of $R^{2a}$, $R^{3a}$, $R^{4a}$, $R^{5a}$ and $R^{6a}$ is other than a hydrogen atom), or two of the adjacent $R^{2a}$, $R^{3a}$, $R^{4a}$, $R^{5a}$ and $R^{6a}$ share a carbon atom to form a carbon ring or a heterocycle (these carbon ring and heterocycle may be optionally substituted), $R^{7a}$ is a hydrogen atom, $R^{8a}$ is a $C_1$-$C_6$ alkyl group or an aryl group, $R^{9a}$ and $R^{10a}$ are each independently a hydrogen atom, a $C_1$-$C_6$ alkyl group, an aryl group or an aryl ($C_1$-$C_6$)alkyl group, $R^{11a}$ is a hydrogen atom or a $C_1$-$C_6$ alkyl group, $X^{1a}$ and $Y^{1a}$ are each independently CH or a nitrogen atom (other than where $X^{1a}$ and $Y^{1a}$ are both CH), $X^{2a}$ and $Y^{2a}$ are both CH, Z is an oxygen atom or a sulfur atom, and n is 0, 1, 2, 3 or 4.

(1-2)

In another embodiment, $R^{1a}$ is a $C_1$-$C_6$ alkyl group, a $C_2$-$C_6$ alkenyl group or a $C_1$-$C_6$ alkoxy group (each of which may be optionally substituted with a halogen atom, $R^{8a}CO$— or $NR^{9a}R^{10a}CO$—), $R^{2a}$, $R^{3a}$, $R^{4a}$, $R^{5a}$ and $R^{6a}$ are each independently a $C_1$-$C_6$ alkyl group, a $C_2$-$C_6$ alkenyl group, a $C_1$-$C_6$ alkoxy group or a $C_1$-$C_6$ alkylthio group (each of which may be optionally substituted with a hydrogen atom, a halogen atom, a nitro group, a cyano group, an aryloxy group, an aryl ($C_1$-$C_6$) alkyloxy group, an aryl ($C_1$-$C_6$)alkyl group, $R^{8a}CO$—, $R^{8a}SO_2NH$—, $R^{8a}CON(R^{11a})$—, $NR^{9a}R^{10a}$—, $NR^{9a}R^{10a}CO$—, —$COOR^{9a}$, a heterocyclic group or a heterocyclic ($C_1$-$C_6$)alkyl group), or two of the adjacent $R^{2a}$, $R^{3a}$, $R^{4a}$, $R^{5a}$ and $R^{6a}$ share a carbon atom to form a carbon ring or a heterocycle (these carbon ring and heterocycle may be optionally substituted), $R^{7a}$ is a hydrogen atom, $R^{8a}$ is a $C_1$-$C_6$ alkyl group or an aryl group, $R^{9a}$ and $R^{10a}$ are each independently a hydrogen atom, a $C_1$-$C_6$ alkyl group, an aryl group or an aryl ($C_1$-$C_6$)alkyl group, $R^{11a}$ is a hydrogen atom or a $C_1$-$C_6$ alkyl group, $X^{1a}$ is CH and $Y^{1a}$ is a nitrogen atom, one of $X^{2a}$ and $Y^{2a}$ is CH while the other is a nitrogen atom, Z is an oxygen atom or a sulfur atom, and n is 0, 1, 2 or 3.

(1-3)

In still another embodiment, $R^{1a}$ is a $C_1$-$C_6$ alkyl group, a $C_2$-$C_6$ alkenyl group or a $C_1$-$C_6$ alkoxy group (each of which may be optionally substituted with a halogen atom, $R^{8a}CO$— or $NR^{9a}R^{10a}CO$—), $R^{2a}$, $R^{3a}$, $R^{4a}$, $R^{5a}$ and $R^{6a}$ are each independently a $C_1$-$C_6$ alkyl group, a $C_2$-$C_6$ alkenyl group, a $C_1$-$C_6$ alkoxy group or a $C_1$-$C_6$ alkylthio group (each of which may be optionally substituted with a hydrogen atom, a halogen atom, a nitro group, a cyano group, an aryloxy group, an aryl ($C_1$-$C_6$) alkyloxy group, an aryl ($C_1$-$C_6$)alkyl group, $R^{8a}CO$—, $R^{8a}SO_2NH$—, $R^{8a}SO_2O$—, $R^{8a}CON(R^{11a})$—, $NR^{9a}R^{10a}$—, $NR^{9a}R^{10a}CO$—, —$COOR^{9a}$, $R^{11a}C(=NOR^{8a})$, a heterocyclic group or a heterocyclic ($C_1$-$C_6$)alkyl group), or two of the adjacent $R^{2a}$, $R^{3a}$, $R^{4a}$, $R^{5a}$ and $R^{6a}$ share a carbon atom to form a carbon ring or a heterocycle (these carbon ring and heterocycle may be optionally substituted), $R^{7a}$ is a $C_1$-$C_6$ alkyl group, a $C_2$-$C_6$ alkenyl group, a $C_1$-$C_6$ alkoxy group or a $C_1$-$C_6$ alkylthio group (each of which may be optionally substituted with a halogen atom, a hydroxyl group, a nitro group, a cyano group, $NR^{9a}R^{10a}$—, $NR^{9a}R^{10a}CO$—, $N_3$, —$OCOR^{9a}$ or $R^{8a}CON(R^{11a})$—), $R^{8a}$ is a $C_1$-$C_6$ alkyl group, a $C_2$-$C_6$ alkenyl group, a heterocyclic group, a heterocyclic ($C_1$-$C_6$)alkyl group, a heterocyclic ($C_2$-$C_6$)alkenyl group, an aryl group, an aryl ($C_1$-$C_6$) alkyl group or an aryl ($C_2$-$C_6$)alkenyl group (each of which may be optionally substituted), $R^{9a}$ and $R^{10a}$ are each independently a hydrogen atom, a $C_1$-$C_6$ alkyl group, a $C_2$-$C_6$ alkenyl group, a heterocyclic group, a heterocyclic ($C_1$-$C_6$)alkyl group, an aryl group or an aryl ($C_1$-$C_6$)alkyl group (each of which may be optionally substituted), $R^{11a}$ is a hydrogen atom or a $C_1$-$C_6$ alkyl group, $X^{1a}$ is CH and $Y^{1a}$ is a nitrogen atom, $X^{2a}$ and $Y^{2a}$ are both CH, Z is an oxygen atom or a sulfur atom, and n is 0, 1, 2 or 3.

(1-4)

In yet still another embodiment, $R^{1a}$ is a $C_1$-$C_6$ alkyl group, a $C_2$-$C_6$ alkenyl group or a $C_1$-$C_6$ alkoxy group (each of which may be optionally substituted with a halogen atom, $R^{8a}CO$— or $NR^{9a}R^{10a}CO$—), $R^{2a}$, $R^{3a}$, $R^{4a}$, $R^{5a}$ and $R^{6a}$ are each independently a $C_1$-$C_6$ alkyl group, a $C_2$-$C_6$ alkenyl group, a $C_1$-$C_6$ alkoxy group or a $C_1$-$C_6$ alkylthio group (each of which is a hydrogen atom, a halogen atom, a nitro group, a cyano group, an aryloxy group, an aryl ($C_1$-$C_6$)alkyloxy group, an aryl ($C_1$-$C_6$)alkyl group, $R^{8a}CO$—, $R^{8a}SO_2NH$—, $R^{8a}SO_2O$—, $R^{8a}CON(R^{11a})$—, $NR^{9a}R^{10a}$—, $NR^{9a}R^{10a}CO$—, —$COOR^{9a}$, $R^{11a}C(=NOR^{8a})$, a heterocyclic group or a heterocyclic ($C_1$-$C_6$) alkyl group), or two of the adjacent $R^{2a}$, $R^{3a}$, $R^{4a}$, $R^{5a}$ and $R^{6a}$ share a carbon atom to form a carbon ring or a heterocycle (these carbon ring and heterocycle may be optionally substituted), $R^{7a}$ is a $C_1$-$C_6$ alkyl group, a $C_2$-$C_6$ alkenyl group, a $C_1$-$C_6$ alkoxy group or a $C_1$-$C_6$ alkylthio group (each of which may optionally by substituted with a halogen atom, a hydroxyl group, a nitro group, a cyano group, $NR^{9a}R^{10a}$—, $NR^{9a}R^{10a}CO$—, $N_3$, —$OCOR^{9a}$ or $R^{8a}CON(R^{11a})$—)

$R^{8a}$ is a $C_1$-$C_6$ alkyl group, a $C_2$-$C_6$ alkenyl group, a heterocyclic group, a heterocyclic ($C_1$-$C_6$)alkyl group, a heterocyclic ($C_2$-$C_6$)alkenyl group, an aryl group, an aryl ($C_1$-$C_6$) alkyl group or an aryl ($C_2$-$C_6$)alkenyl group (each of which may be optionally substituted), $R^{9a}$ and $R^{10a}$ are each independently a hydrogen atom, a $C_1$-$C_6$ alkyl group, a $C_2$-$C_6$ alkenyl group, a heterocyclic ($C_1$-$C_6$)alkyl group, an aryl group or an aryl ($C_1$-$C_6$)alkyl group (each of which may be optionally substituted), $R^{11a}$ is a hydrogen atom or a $C_1$-$C_6$ alkyl group, $X^{1a}$ is CH and $Y^{1a}$ is a nitrogen atom, one of $X^{2a}$ and $Y^{2a}$ is CH while the other is a nitrogen atom, Z is an oxygen atom or a sulfur atom, and n is 0, 1, 2 or 3.

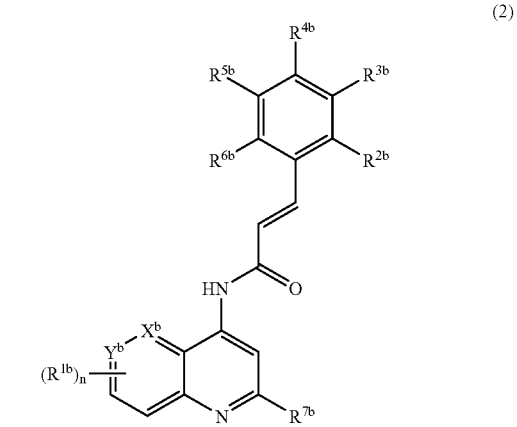

(2)

In formula (2), $R^{1b}$ is a $C_1$-$C_6$ alkyl group, a $C_2$-$C_6$ alkenyl group or a $C_1$-$C_6$ alkoxy group (each of which may be optionally substituted with a halogen atom, $R^{8b}CO$— or $NR^{9b}R^{10b}CO$—), $R^{2b}$, $R^{3b}$, $R^{4b}$, $R^{5b}$ and $R^{6b}$ are each independently a $C_1$-$C_6$ alkyl group, a $C_2$-$C_6$ alkenyl group, a $C_1$-$C_6$ alkoxy group or a $C_1$-$C_6$ alkylthio group (each of which may be optionally substituted with a hydrogen atom, a halogen atom, a nitro group, a cyano group, an aryloxy group, an aryl ($C_1$-$C_6$) alkyloxy group, an aryl ($C_1$-$C_6$)alkyl group, $R^{8b}CO$—, $R^{8b}SO_2NH$—, $R^{8b}SO_2O$—, $R^{8b}CON(R^{11b})$—, $NR^{9b}R^{10b}$—, $NR^{9b}R^{10b}CO$—, —$COOR^{9b}$, $R^{11b}C(=NOR^{8b})$, a heterocyclic group or a heterocyclic ($C_1$-$C_6$)alkyl group), or two of the adjacent $R^{2b}$, $R^{3b}$, $R^{4b}$, $R^{5b}$ and $R^{6b}$ share a carbon atom to form a carbon ring or a heterocycle (these carbon ring and heterocycle may be optionally substituted), $R^{7b}$ is a hydrogen atom, a $C_1$-$C_6$ alkyl group, a $C_2$-$C_6$ alkenyl group, a $C_1$-$C_6$ alkoxy group or a $C_1$-$C_6$ alkylthio group (each of which may optionally be substituted with a halogen atom, a hydroxyl group, a nitro group, a cyano group, $NR^{9b}R^{10b}$—, $NR^{9b}R^{10b}CO$—, $N_3$, —$OCOR^{9b}$ or $R^{8b}CON(R^{11b})$—), $R^{8b}$ is a $C_1$-$C_6$ alkyl group, a $C_2$-$C_6$ alkenyl group, a heterocyclic group, a heterocyclic ($C_1$-$C_6$)alkyl group, an aryl group or an aryl ($C_1$-$C_6$)alkyl group (each of which may be optionally substituted), $R^{9b}$ and $R^{10b}$ are each independently a hydrogen atom, a $C_1$-$C_6$ alkyl group, a $C_2$-$C_6$ alkenyl group, a heterocyclic group, a heterocyclic ($C_1$-$C_6$)alkyl group, an aryl group or an aryl ($C_1$-$C_6$)alkyl group (each of which may be optionally substituted), $R^{11b}$ is a hydrogen atom or a $C_1$-$C_6$ alkyl group, $X^b$ and $Y^b$ are each independently CH or a nitrogen atom (other than where both of $X^b$ and $Y^b$ are nitrogen atoms), n is 0, 1, 2, 3 or 4 when $X^b$ and $Y^b$ are both CH while 0, 1, 2 or 3 when one of $X^b$ and $Y^b$ is CH and the other is a nitrogen atom.

The compound represented by formula (2) can be obtained by but not limited to the process described in WO 00/47576, or a process pursuant thereto.

(3)

In formula (3)

$R^{1c}$, $R^{2c}$, $R^{3c}$, and $R^{4c}$ are each independently a cyano group, a nitro group, a halogen atom, a hydrogen atom, a hydroxyl group, a $C_1$-$C_6$ alkyl group, a $C_2$-$C_6$ alkenyl group, a $C_1$-$C_6$ alkoxy group, a $C_2$-$C_6$ alkenyloxy group, a trifluoromethyl group, a trifluoromethoxy group, a cycloalkyloxy group, an aryloxy group, an aralkyloxy group, a heterocyclic oxy group, a heterocyclic alkyloxy group, $R^{11c}CO$—, $NR^{12c}R^{13c}CO$—, $R^{12c}R^{13c}N$—, $R^{11c}OOC$—, $R^{11c}SO_2NH$— or $R^{14c}$—CO—NH—; or $R^{2c}$ and $R^{3c}$, $R^{1c}$ and $R^{2c}$ or $R^{3c}$ and $R^{4c}$ fuse with a phenyl ring to form a 5-membered ring, a 6-membered ring or a 7-membered ring containing one or two oxygen atoms, $R^{5c}$, $R^{6c}$, $R^{7c}$, $R^{8c}$, $R^{9c}$ and $R^{10c}$ are each independently a hydrogen atom, an aryl group, an aralkyl group, a $C_1$-$C_6$ alkyl group, a $C_2$-$C_6$ alkenyl group, a trifluoromethyl group, a cycloalkyl group, a heterocyclic group or a heterocyclic ($C_1$-$C_6$)alkyl group, $R^{11c}$ is a $C_1$-$C_6$ alkyl group, an aryl group, an aralkyl group, a heterocyclic group or a heterocyclic ($C_1$-$C_6$)alkyl group, $R^{12c}$ and $R^{13c}$ are each independently hydrogen atom, an alkyl group, a cycloalkyl group, an aryl group, an aralkyl group, a heterocyclic group or a heterocyclic ($C_1$-$C_6$)alkyl group, and $R^{14c}$ is an alkyl group, an aryl group, a cycloalkyl group, a heterocyclic group, $R^{12c}R^{13c}N$— or $R^{11c}O$—.

The compound represented by formula (3) may be, for example, but without limitation, an optically pure enantiomer, an enantiomer mixture, a racemic compound (a racemic mixture), an optically pure diastereoisomer, a diastereoisomer mixture, a diastereoisomer racemic compound, a diastereoisomer racemic compound mixture or a meso compound.

The compound represented by formula (3) can be obtained by but not limited to the process described in WO 01/68609, or a process pursuant thereto.

(4)

In formula (4), $R^{1d}$, and $R^{2d}$ are each independently a hydrogen atom, a hydroxyl group, a methoxy group or a halogen atom, or they fuse with a phenyl ring to form a 5-membered ring, a 6-membered ring or a 7-membered ring containing one or two oxygen atoms, and $R^{3d}$, $R^{4d}$ and $R^{5d}$ are each independently an aryl group, an aralkyl group, a $C_1$-$C_6$ alkyl group, a $C_2$-$C_6$ alkenyl group, a trifluoromethyl group, a cycloalkyl group, a heterocyclic group or a heterocyclic ($C_1$-$C_6$)alkyl group.

The compound represented by formula (4) may be, for example, but without limitation, an optically pure enantiomer, an enantiomer mixture, a racemic compound (a racemic mixture), an optically pure diastereoisomer, a diastereoisomer mixture, a diastereoisomer racemic compound, a diastereoisomer racemic compound mixture or a meso compound.

The compound represented by formula (4) can be obtained by but not limited to the process described in WO 01/68609, or a process pursuant thereto.

(5)

In formula (5), $R^{1e}$, $R^{2e}$, $R^{3e}$ and $R^{4e}$ are each independently a cyano group, a nitro group, a halogen atom, a hydrogen atom, a hydroxyl group, a $C_1$-$C_6$ alkyl group, a $C_2$-$C_6$ alkenyl group, a $C_1$-$C_6$ alkoxy group, a $C_2$-$C_6$ alkenyloxy group, a trifluoromethyl group, a trifluoromethoxy group, a cycloalkyloxy group, an aryloxy group, an aralkyloxy group, a heterocyclic oxy group, a heterocyclic alkyloxy group, $R^{11e}CO$—, $NR^{12e}R^{13e}CO$—, $R^{12e}R^{13e}N$—, $R^{11e}OOC$—, $R^{11e}SO_2NH$— or $R^{14e}$—CO—NH—; or $R^{2e}$ and $R^{3e}$, $R^{1e}$ and $R^{2e}$ or $R^{3e}$ and $R^{4e}$ fuse with a phenyl ring to form a 5-membered ring, a 6-membered ring or a 7-membered ring containing one or two oxygen atoms, $R^{5e}$ is an aryl group, an aralkyl group, a $C_1$-$C_6$ alkyl group, a $C_2$-$C_6$ alkenyl group, a trifluoromethyl group, a cycloalkyl group, a heterocyclic group or a heterocyclic ($C_1$-$C_6$)alkyl group, $R^{6e}$ is a hydrogen atom, an aryl group, an aralkyl group, a $C_1$-$C_6$ alkyl group, a $C_2$-$C_6$ alkenyl group, a trifluoromethyl group, a cycloalkyl group, a heterocyclic group or a heterocyclic ($C_1$-$C_6$)alkyl group, $R^{7e}$ and $R^{8e}$ are each independently a hydrogen atom, an aryl group, an aralkyl group, a $C_1$-$C_6$ alkyl group, a $C_2$-$C_6$ alkenyl group, a cycloalkyl group, a heterocyclic group or a heterocyclic ($C_1$-$C_6$)alkyl group, $R^{9e}$ and $R^{10e}$ are each independently a hydrogen atom, an aryl group, an aryl cycloalkyl group, an aralkyl group, a $C_1$-$C_6$ alkyl group, a $C_2$-$C_6$ alkenyl group, a $C_3$-$C_6$ alkynyl group, a cycloalkyl group, a heterocyclic group or a heterocyclic ($C_1$-$C_6$)alkyl group (each of which may optionally have one, several or all of hydrogen atoms substituted with a halogen atom, or one or two hydrogen atoms substituted with a hydroxyl group, a nitro group, a cyano group, a trifluoromethyl group, a trifluoromethoxy group, a —O—($C_1$-$C_6$)alkyl group, a —NH—($C_1$-$C_6$)alkyl group, —N($C_1$-$C_6$ alkyl)$_2$, a —S—($C_1$-$C_6$)alkyl group, a —COO—($C_1$-$C_6$)alkyl group, a —CONH—($C_1$-$C_6$)alkyl group, a —CON($C_1$-$C_6$ alkyl)$_2$, a —CO—($C_1$-$C_6$)alkyl group, a —NHCO—($C_1$-$C_6$)alkyl group, a —O—($C_3$-$C_5$)alkenyl group, a —NH—($C_3$-$C_5$)alkenyl group, a —N($C_3$-$C_5$ alkenyl)$_2$, a —S—($C_3$-$C_5$)alkenyl group, a —COO—($C_3$-$C_5$)alkenyl group, a —CONH—($C_3$-$C_5$)alkenyl group, —CON($C_3$-$C_5$ alkenyl)$_2$, a —CO—($C_3$-$C_5$)alkenyl group, a —NHCO—($C_3$-$C_5$)alkenyl group, a —O—($C_3$-$C_5$)alkynyl group, a —NH—($C_3$-$C_5$)alkynyl group, —N($C_3$-$C_5$ alkynyl)2, a —S—($C_3$-$C_5$)alkynyl group, a —COO—($C_3$-$C_5$)alkynyl group, a —CONH—($C_3$-$C_5$) alkynyl group, —CON($C_3$-$C_5$ alkynyl)$_2$, a —CO—($C_3$-$C_5$) alkynyl group or a NHCO—($C_3$-$C_5$)alkynyl group), $R^{11e}$ is a $C_1$-$C_6$ alkyl group, an aryl group, an aralkyl group, a heterocyclic group or a heterocyclic ($C_1$-$C_6$)alkyl group, $R^{12e}$ and $R^{13e}$ are each independently a hydrogen atom, a $C_1$-$C_6$ alkyl group, a cycloalkyl group, an aryl group, an aralkyl group, a heterocyclic group or a heterocyclic ($C_1$-$C_6$) alkyl group, $R^{14e}$ is a $C_1$-$C_6$ alkyl group, an aryl group, a cycloalkyl group, a heterocyclic group, $R^{12e}R^{3e}N$— or $R^{11e}O$—, —$X^e$—$Y^e$— is —$CH_2$—$CH_2$—, —O—$CH_2$—, —S—$CH_2$—, —$SO_2$—$CH_2$— or $NR^{15e}$—CO—, and $R^{15e}$ is a hydrogen atom, a $C_1$-$C_6$ alkyl group or an aralkyl group.

The compound represented by formula (5) may be, for example, but without limitation, an optically pure enantiomer, an enantiomer mixture, a racemic compound (a racemic mixture), an optically pure diastereoisomer, a diastereoisomer mixture, a diastereoisomer racemic compound, a diastereoisomer racemic compound mixture or a meso compound.

The compound represented by formula (5) can be obtained by but not limited to the process described in WO 02/51838, or a process pursuant thereto.

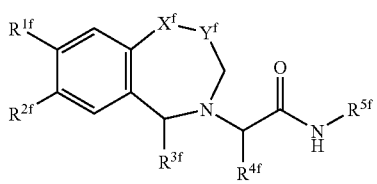

(6)

In formula (6), $R^{1f}$ and $R^{2f}$ are each independently a hydrogen atom, a hydroxyl group, a $C_1$-$C_6$ alkoxy group, a $C_2$-$C_6$ alkenyloxy group or a halogen atom, or they may fuse with a phenyl ring to form a 5-membered ring, 6-membered ring or 7-membered ring containing one or two oxygen atoms, $R^{3f}$ is an aryl group, an aralkyl group, a $C_1$-$C_6$ alkyl group, a $C_2$-$C_6$ alkenyl group, a cycloalkyl group, a heterocyclic group or a heterocyclic ($C_1$-$C_6$)alkyl group, $R^{4f}$ and $R^{5f}$ are each independently a hydrogen atom, an aryl group, an aralkyl group, a $C_1$-$C_6$ alkyl group, a $C_2$-$C_6$ alkenyl group, a cycloalkyl group, a heterocyclic group or a heterocyclic ($C_1$-$C_6$)alkyl group, —$X^f$—$Y^f$— is —$CH_2$—$CH_2$—, —O—$CH_2$—, —S—$CH_2$—, —$SO_2$—$CH_2$— or $NR^{6f}$—CO, and $R^{6f}$ is a hydrogen atom, a $C_1$-$C_6$ alkyl group or an aralkyl group.

The compound represented by formula (6) may be, for example, but without limitation, an optically pure enantiomer, an enantiomer mixture, a racemic compound (a racemic mixture), an optically pure diastereoisomer, a diastereoisomer mixture, a diastereoisomer racemic compound, a diastereoisomer racemic compound mixture or a meso compound.

The compound represented by formula (6) can be obtained by but not limited to the process described in WO 02/51838, or a process pursuant thereto.

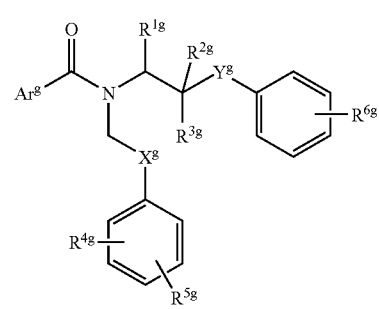

(7)

In formula (7), $R^{1g}$ is a hydrogen atom, $R^{2g}$ is a $C_1$-$C_3$alkyl group and $R^{3g}$ hydrogen atom or a $C_1$-$C_3$ alkyl group, or $R^2$ and $R^{3g}$ carbon atom to form a $C_3$-$C_5$ cycloalkyl group, or:

$R^{1g}$ is a $C_1$-$C_3$ alkyl group, $R^{2g}$ is a hydrogen atom and $R^{3g}$ is a hydrogen atom or a $C_1$-$C_3$ alkyl group, $R^{4g}$ and $R^{5g}$ are each independently selected from a hydrogen atom, a halogen atom, a cyano group, an optionally substituted $C_1$-$C_6$ alkyl CO—, an optionally substituted $C_1$-$C_6$ alkyl group, an optionally substituted $C_1$-$C_6$ alkoxy group, an optionally substituted $C_1$-$C_6$ alkyl OCO—, and an optionally substituted $C_1$-$C_6$ alkyl NHCO— (other than where both $R^{4g}$ and $R^{5g}$ are hydrogen atoms), $R^{6g}$ is a hydrogen atom or a halogen atom, $Ar^g$ is an aryl group which may be optionally substituted, or an aromatic heterocyclic group of a 5-membered ring or a 6-membered ring containing three or less hetero atoms selected from N, O and S (where the aromatic heterocyclic group may be optionally substituted), or $Ar^g$ is a bicyclic heteroaryl group containing three or less hetero atoms selected from N, O and S (where the heteroaryl group may be optionally substituted), $X^g$ is —$CH_2$— or a single bond, and $Y^g$ is —NHCO— or a single bond.

The compound represented by formula (7) can be obtained by but not limited to the process described in WO 03/37847, or a process pursuant thereto.

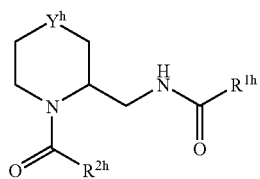

(8)

In formula (8), $Y^h$ is an oxygen atom or $(CH_2)_n$ (where n is 0, 1 or 2), $R^{1h}$ is a phenyl group, a naphthyl group, a monocyclic or bicyclic heteroaryl group containing three or less hetero atoms selected from N, O and S, or a $NR^{3h}R^{4h}$ group (where one of $R^{3h}$ and $R^{4h}$ is a hydrogen atom or an optionally substituted $C_1$-$C_4$ alkyl group and the other is a phenyl group, a naphthyl group, or a monocyclic or bicyclic heteroaryl group containing three or less hetero atoms selected from N, O and S, or $R^{3h}$ and $R^{4h}$ are a cyclic amine of a 5-membered ring, a 6-membered ring or a 7-membered ring sharing a nitrogen atom optionally fusing with a phenyl ring) (each of which may be optionally substituted), $R^{2h}$ is a phenyl group, or a heteroaryl group of a 5-membered ring or a 6-membered ring containing three or less hetero atoms selected from N, O and S (where the phenyl group or the heteroaryl group may be substituted with $R^{5h}$ and further optionally substituents), or $R^{2h}$ is an optionally substituted bicyclic aromatic ring group or bicyclic heteroaromatic ring group containing three or less hetero atoms selected from N, O and S, $R^{5h}$ is an optionally substituted $C_1$-$C_4$ alkoxy group, a halogen atom, an optionally substituted $C_1$-$C_6$ alkyl group, an optionally substituted phenyl group, or a heterocyclic group of an optionally substituted 5-membered ring or 6-membered ring containing three or less hetero atoms selected from N, O and S.

The compound represented by formula (8) can be obtained by but not limited to the process described in WO 01/96302 or WO 02/44172, or a process pursuant thereto. Specifically, the following embodiments (8-1) and (8-2) are illustrated as preferable embodiments for formula (8).

(8-1)

In one embodiment, $Y^h$ is $(CH_2)_n$ (where n is 0, 1 or 2), $R^{1h}$ is a phenyl group, a naphthyl group, a monocyclic or bicyclic heteroaryl group containing three or less hetero atoms selected from N, O and S, or a $NR^{3h}R^{4h}$ group (where one of $R^{3h}$ and $R^{4h}$ is a hydrogen atom or an optionally substituted $C_1$-$C_4$ alkyl group while the other is a phenyl group, a naphthyl group, or a monocyclic or bicyclic heteroaryl group containing three or less hetero atoms selected from N, O and S, or $R^{3h}$ and $R^{4h}$ are a cyclic amine of a 5-membered ring, a 6-membered ring or a 7-membered ring sharing a nitrogen atom and optionally fusing with a phenyl ring) (each of which may be optionally substituted), $R^{2h}$ is a phenyl group, or a heteroaryl group of a 5-membered ring or a 6-membered ring containing three or less hetero atoms selected from N, O and S (where the phenyl group or the heteroaryl group may be substituted with $R^{5h}$ and further optionally substituents), or $R^{2h}$ is an optionally substituted bicyclic aromatic ring group, or an optionally substituted bicyclic aromatic ring group or bicyclic heteroaromatic ring group containing three or less hetero atoms selected from N, O and S, $R^{5h}$ is an optionally substituted $C_1$-$C_4$ alkoxy group, a halogen atom, an optionally substituted $C_1$-$C_6$ alkyl group, an optionally substituted phenyl group, or a heterocyclic group of an optionally substituted 5-membered ring or 6-membered ring containing three or less hetero atoms selected from N, O and S.

(8-2)

In another embodiment, $Y^h$ is an oxygen atom, $R^{1h}$ is a phenyl group, a naphthyl group, or a monocyclic or bicyclic heteroaryl group containing three or less hetero atoms selected from N, O and S (each of which may be optionally substituted), $R^{2h}$ is a phenyl group, or a heteroaryl group of a 5-membered ring or a 6-membered ring containing three or less hetero atoms selected from N, O and S (where the phenyl group or the heteroaryl group may be substituted with $R^{5h}$ and further optionally substituents), or $R^{2h}$ is an optionally substituted bicyclic aromatic ring group, or an optionally substituted bicyclic aromatic ring group or bicyclic heteroaromatic ring group containing three or less hetero atoms selected from N, O and S, $R^{5h}$ is an optionally substituted $C_1$-$C_4$ alkoxy group, a halogen atom, an optionally substituted $C_1$-$C_6$ alkyl group, an optionally substituted phenyl group, or a heterocyclic group of an optionally substituted 5-membered ring or 6-membered ring containing three or less hetero atoms selected from N, O and S.

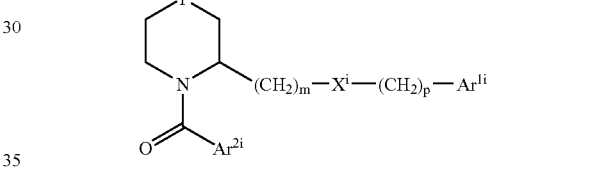

(9)

In formula (9), $Y^i$ is a single bond, an oxygen atom, $(CH_2)_n$ (where n is 1, 2 or 3) or $NR^{2i}$, m is 1, 2 or 3, p is 0 or 1, $X^i$ is O, S, C=O, $SO_2$, —CH=CH—, NH or $N(C_1$-$C_4)$ alkyl, $Ar^{1i}$ is an aryl group, or a monocyclic or bicyclic heteroaryl group containing four or less heteroatoms selected from N, O and S (each of which may be optionally substituted), $Ar^{2i}$ is a phenyl group, or a heterocyclic group of a 5-membered ring or a 6-membered ring containing three or less hetero atoms selected from N, O and S (where the phenyl group or the heterocyclic group may be substituted with $R^{1i}$ and further optionally substituents), or $Ar^{2i}$ is an optionally substituted bicyclic aromatic group or heteroaromatic group containing four or less hetero atoms selected from N, O and S, $R^{1i}$ is a hydrogen atom, an optionally substituted $C_1$-$C_4$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less heteroatoms selected from N, O and S, $R^{2i}$ is a hydrogen atom, an optionally substituted $C_1$-$C_4$ alkyl group, an optionally substituted $C_1$-$C_6$ alkanoyl group, an optionally substituted $C_1$-$C_6$ alkanoxycarbonyl group, or an optionally substituted $C_1$-$C_6$ alkylaryloxycarbonyl group.

The compound represented by formula (9) can be obtained by but not limited to the process described in WO 02/89800, WO 02/90355 or WO 03/32991, or a process pursuant thereto. Specifically, the following embodiments (9-1) to (9-3) are illustrated as preferable embodiments for formula (9).

(9-1)

In one embodiment, $Y^i$ is a single bond, an oxygen atom, or $(CH_2)_n$ (where n is 1, 2 or 3), m is 1, 2 or 3, p is 0 or 1, $X^i$ is O, S, C=O, SO$_2$ or —CH=CH—, $Ar^{1i}$ is an aryl group, or a monocyclic or bicyclic heteroaryl group containing four or less heteroatoms selected from N, O and S (each of which may be optionally substituted), $Ar^{2i}$ is a phenyl group, or a heterocyclic group of a 5-membered ring or a 6-membered ring containing three or less hetero atoms selected from N, O and S (where the phenyl group or the heterocyclic group may be substituted with $R^{1i}$ and further optionally substituents), or $Ar^{2i}$ is an optionally substituted bicyclic aromatic group or heteroaromatic group containing three or less hetero atoms selected from N, O and S, and $R^{1i}$ is a hydrogen atom, an optionally substituted $C_1$-$C_4$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less hetero atoms selected from N, O and S.

(9-2)

In another embodiment, $Y^i$ is a single bond, an oxygen atom or $(CH_2)_n$ (where n is 1, 2or 3), m is 1, 2 or 3, p is 0 or 1, $X^i$ is NH or N($C_1$-$C_4$) alkyl, $Ar^{1i}$ is an aryl group, or a monocyclic or bicyclic heteroaryl group containing three or less heteroatoms selected from N, O and S (each of which may be optionally substituted), $Ar^{2i}$ is a phenyl group, or a heterocyclic group of a 5-membered ring or a 6-membered ring containing three or less hetero atoms selected from N, O and S (where the phenyl group or the heterocyclic group may be substituted with $R^{1i}$ and further optionally substituents), or $Ar^{2i}$ is an optionally substituted bicyclic aromatic group or heteroaromatic group containing three or less hetero atoms selected from N, O and S, $R^{1i}$ is a hydrogen atom, an optionally substituted $C_1$-$C_4$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less hetero atoms selected from N, O and S.

(9-3)

In yet still another embodiment, $Y^i$ is $NR^{2i}$, m is 1, 2 or 3, p is 0 or 1, $X^i$ is O, S, C=O, SO$_2$ or —CH=CH—, $Ar^{1i}$ is an aryl group, or a monocyclic or bicyclic heteroaryl group containing four or less heteroatoms selected from N, O and S (each of which may be optionally substituted), $Ar^{2i}$ is a phenyl group, or a heterocyclic group of a 5-membered ring or a 6-membered ring containing three or less hetero atoms selected from N, O and S (where the phenyl group or the heterocyclic group may be substituted with $R^{1i}$ and further optionally substituents), or $Ar^{2i}$ is an optionally substituted bicyclic aromatic group or heteroaromatic group containing four or less hetero atoms selected from N, O and S, $R^{1i}$ is an optionally substituted $C_1$-$C_4$ alkoxy group, a halogen atom, an optionally substituted $C_1$-$C_6$ alkyl group, an optionally substituted phenyl group, or a heterocyclic group of an optionally substituted 5-membered ring or 6-membered ring containing four or less hetero atoms selected from N, O and S, and $R^{2i}$ is a hydrogen atom, an optionally substituted $C_1$-$C_4$ alkyl group, an optionally substituted $C_1$-$C_6$ alkanoyl group, an optionally substituted $C_1$-$C_6$ alkanoxycarbonyl group, or an optionally substituted $C_1$-$C_6$ alkylaryloxycarbonyl group.

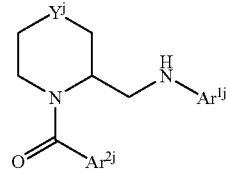

(10)

In formula (10), $Y^j$ is a single bond, an oxygen atom or $(CH_2)_n$ (where n is 1, 2 or 3), $Ar^{1j}$ is an optionally substituted monocyclic or bicyclic heteroaryl group containing three or less heteroatoms selected from N, O and S, $Ar^{2j}$ is a phenyl group, or a heterocyclic group of a 5-membered ring or a 6-membered ring containing three or less hetero atoms selected from N, O and S (where the phenyl group or the heterocyclic group may be substituted with $R^{1j}$ and further optionally substituents), or $Ar^{2j}$ is an optionally substituted bicyclic aromatic group or bicyclic heteroaromatic group containing three or less hetero atoms selected from N, O and S, $R^{1j}$ is a hydrogen atom, an optionally substituted $C_1$-$C_4$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less hetero atoms selected from N, O and S, and $Ar^{2j}$ is not a 2-naphthyl group when $Y^j$ is a single bond.

The compound represented by formula (10) can be obtained by but not limited to the process described in WO 02/90355, or a process pursuant thereto.

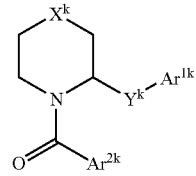

(11)

In formula (11), $X^k$ is a single bond, an oxygen atom, $NR^{3k}$ or $(CH_2)_n$ (where n is 1, 2 or 3), $Y^k$ is $CH_2$, CO, CH(OH) or —CH$_2$CH(OH)—, $A^{1k}$ is an optionally substituted bicyclic heteroaryl group containing four or less hetero atoms selected from N, O and S, or a monocyclic heteroaryl group of a 5-membered ring or a 6-membered ring containing four or less hetero atoms selected from N, O and S (where the monocyclic heteroaryl group may optionally be substituted (for example, at least with $R^{2k}$)), $Ar^{2k}$ is a phenyl group, a heterocyclic group of a 5-membered ring or a 6-membered ring containing three or less hetero atoms selected from N, O and S, or a heteroaryl group of a 5-membered ring or a 6-membered ring containing three or less hetero atoms selected from N, O and S (where the phenyl group, the heterocyclic group or the heteroaryl group may optionally be substituted (for example, with $R^{1k}$ and further optionally substituents), or $Ar^{2k}$ is an optionally substituted bicyclic aromatic group or heteroaromatic group containing three or less hetero atoms selected from N, O and S, $R^{1k}$ is a hydrogen atom, an optionally substituted $C_1$-$C_4$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less heteroatoms selected from N, O and S, $R^{2k}$ is an optionally substituted aryl group, or an optionally substituted monocyclic or bicyclic heteroaryl group containing three or less hetero atoms selected from N, O and S, and $R^{3k}$ is a hydrogen atom, or an optionally substituted $C_1$-$C_4$ alkyl group.

The compound represented by formula (11) can be obtained by but not limited to the process described in WO 03/2559 or WO 03/2561, or a process pursuant thereto. Specifically, the following embodiments (11-1) and (11-2) are illustrated as preferable embodiments for formula (11).

(11-1)

In one embodiment, $X^k$ is a single bond, an oxygen atom, $NR^{3k}$ or $(CH_2)_n$ (where n is 1, 2 or 3), $Y^k$ is $CH_2$, CO, CH(OH) or —$CH_2CH(OH)$—, $Ar^{1k}$ is a monocyclic heteroaryl group of a 5-membered ring or a 6-membered ring containing four or less hetero atoms selected from N, O and S (where the heteroaryl group may be substituted with at least $R^{2k}$), $Ar^{2k}$ is a phenyl group, or a heteroaryl group of a 5-membered ring or a 6-membered ring containing three or less hetero atoms selected from N, O and S (where the phenyl group or the heteroaryl group may be substituted with at least $R^{1k}$ and further optionally substituents), or $Ar^{2k}$ is an optionally substituted bicyclic aromatic group or heteroaromatic group containing three or less hetero atoms selected from N, O and S, $R^{1k}$ hydrogen atom, an optionally substituted $C_1$-$C_4$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less heteroatoms selected from N, O and S, $R^{2k}$ is an optionally substituted aryl group, or an optionally substituted monocyclic or bicyclic heteroaryl group containing three or less hetero atoms selected from N, O and S, and $R^{3k}$ is a hydrogen atom or a $C_1$-$C_4$ alkyl group.

(11-2)

In another embodiment, $X^k$ is a single bond, an oxygen atom, $NR^{3k}$ or $(CH_2)_n$ (wherein is 1, 2 or 3), $Y^k$ is $CH_2$, CO, CH(OH) or —$CH_2CH(OH)$—, $Ar^{1k}$ is an optionally substituted bicyclic heteroaryl group containing four or less heteroatoms selected from N, O and S, $Ar^{2k}$ is a phenyl group, or a heterocyclic group of a 5-membered ring or a 6-membered ring containing three or less hetero atoms selected from N, O and S (where the phenyl group or the heterocyclic group may optionally be substituted with at least $R^{1k}$ and further optionally substituents), or $Ar^{2k}$ is an optionally substituted bicyclic aromatic group or heteroaromatic group containing three or less hetero atoms selected from N, O and S, $R^{1k}$ is a hydrogen atom, an optionally substituted $C_1$-$C_4$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less heteroatoms selected from N, O and S, $R^{3k}$ is a hydrogen atom or a $C_1$-$C_4$ alkyl group when $Ar^{1k}$ is indolyl, or a hydrogen atom or an optionally substituted $C_1$-$C_4$ alkyl group when $Ar^{1k}$ is other than indolyl, and $Ar^{2k}$ is not 3,5-bis(trifluoromethyl)phenyl when $X^k$ is NH, $Y^k$ is $CH_2$ and $Ar^{1k}$ is indolyl.

In the case of (11-2), the compound represented by formula (11) is a compound other than (2R)-1-(3,5-dichlorobenzoyl)-2-[(1H-indole-3-yl)methyl]piperazine, (2R)-2-[(1H-indole-3-yl)methyl]-1-[(3-methoxy-5-trifluoromethyl)benzoyl]piperazine and 1-benzoyl-2-[(1H-indole-3-yl)methyl]piperazine.

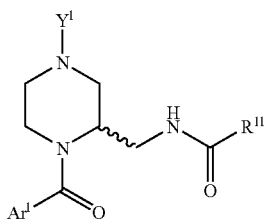

(12)

In formula (12), $Y^1$ is a hydrogen atom or a $C_1$-$C_6$ alkyl group, $R^{11}$ is an optionally substituted aryl group, or a heterocyclic group of an optionally substituted 5-membered ring or 6-membered ring containing four or less heteroatoms selected from N, O and S, $Ar^1$ is an aryl group, or a heterocyclic group of a 5-membered ring or a 6-membered ring containing three or less hetero atoms selected from N, O and S (where the aryl group or the heterocyclic group may be substituted with $R^{21}$ and further optionally substituents), and $R^{21}$ is an optionally substituted $C_1$-$C_6$ alkoxy group, a halogen atom, a cyano group, an optionally substituted $C_1$-$C_6$ alkyl group, an optionally substituted phenyl group, or a heterocyclic group of an optionally substituted 5-membered ring or 6-membered ring containing four or less hetero atoms selected from N, O and S.

The compound represented by formula (12) can be obtained by but not limited to the process described in WO 03/41711, or a process pursuant thereto.

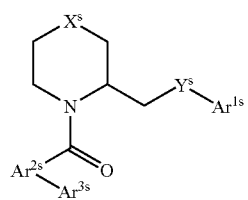

(13)

In formula (13), $X^s$ is a single bond, an oxygen atom, $NR^{3s}$ or $(CH_2)_n$, (where n is 1 or 2), $Y^s$ is —$(CH_2)_qNHC(O)$, —$(CH_2)_qO(CH_2)_p$, —$(CH_2)_qS(CH_2)_p$, —$(CH_2)_qC(O)(CH_2)_p$, —$(CH_2)_qSO_2(CH_2)_p$, —$(CH_2)_qCH=CH(CH_2)_p$, —$(CH_2)_qCH(OH)(CH_2)_p$, —C(O), $(CH_2)_3$, —$(CH_2)_qNH$, —$(CH_2)_qNHCONH$ or $(CH_2)_qCONH$ (where q is 1 or 2, and p is 0 or 1), $Ar^{1s}$ is a phenyl group, a naphthyl group, or a heteroaryl group of a 5-membered ring or a 6-membered ring containing three or less heteroatoms selected from N, O and S, or a bicyclic heteroaryl group containing three or less heteroatoms selected from N, O and S, $Ar^{2s}$ is an optionally substituted phenyl group, or a heteroaryl group of a 5-membered ring or a 6-membered ring containing three or less heteroatoms selected from N, O and S, $Ar^{3s}$ is an optionally substituted group represented by the following formula:

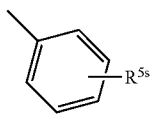

where $R^{5s}$ is $—O(CH_2)_mNR^{1s}R^{2s}$ or $(CH_2)_mNR^{1s}R^{2s}$, and m is an integer of 2 to 6, $R^{1s}$ and $R^{2s}$ are each independently a hydrogen atom, or an optionally substituted $C_1$-$C_6$ alkyl group, or $R^{1s}$ and $R^{2s}$ share a nitrogen atom to form a part of a $C_3$-$C_6$ azacycloalkane ring or a $C_3$-$C_6$ (2-oxo)azacycloalkane ring, or, $R^{1s}$ forms a $C_3$-$C_6$ azacycloalkane ring or a $C_3$-$C_6$ (2-oxo) azacycloalkane ring with at least one $CH_2$ of the $(CH_2)_m$ moiety of $R^{5s}$, and $R^{2s}$ forms a second $C_3$-$C_6$ azacycloalkane ring that fuses with a first $C_3$-$C_6$ azacycloalkane ring, with a hydrogen atom, an optionally substituted $C_1$-$C_6$ alkyl group, a piperidine group, a pyrrolidine group, a morpholine group or a nitrogen atom, $R^{3s}$ is a hydrogen atom, or an optionally substituted $C_1$-$C_6$ alkyl group, and $Ar^{3s}$ binds to $Ar^{2s}$ in ortho-position to an amide carbonyl group.

The compound represented by formula (13) can be obtained by but not limited to the process described in WO 03/51368, or a process pursuant thereto.

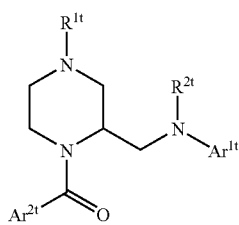

(14)

In formula (14), $R^{1t}$ and $R^{2t}$ are each independently a hydrogen atom, or an optionally substituted $C_1$-$C_6$ alkyl group, $Ar^{1t}$ is a heteroaryl group of an optionally substituted 5-membered ring or 6-membered ring containing three or less heteroatoms selected from N, O and S, or an optionally substituted bicyclic heteroaryl group containing three or less heteroatoms selected from N, O and S, $Ar^{2t}$ is a phenyl group, or a heteroaryl group of a 5-membered ring or a 6-membered ring containing three or less hetero atoms selected from N, O and S (where the phenyl group or the heteroaryl group may be substituted with $R^{3t}$ and further optionally substituents), or $Ar^{2t}$ is an optionally substituted bicyclic aromatic group or heteroaromatic group containing three or less hetero atoms selected from N, O and S, and $R^{3t}$ is an independently a hydrogen atom, or an hydrogen atom, an optionally substituted $C_1$-$C_4$ alkoxy group, a halo-gen atom, an optionally substituted $C_1$-$C_6$ alkyl group, an optionally substituted phenyl group, or a heterocyclic group of an optionally substituted 5-membered ring or 6-membered ring containing three or less hetero atoms selected from N, O and S.

The compound represented by formula (14) can be obtained by but not limited to the process described in WO 03/51873, or a process pursuant thereto.

Preferably, a pharmacologically acceptable salt of an orexin receptor antagonist (hereinafter, also referred to as "a salt of an orexin receptor antagonist") includes but not limited to hydrogen halide salts (e.g., hydrochloride, hydrobromate and hydroiodide), inorganic acid salts (e.g., sulfate, nitrate, perchlorate, phosphate, carbonate and bicarbonate), organic carboxylates (e.g., acetate, trifluoroacetate, maleate, tartrate, fumarate and citrate), organic sulfonates (e.g., methanesulfonate, trifluoromethanesulfonate, ethane sulfonate, benzenesulfonate, toluenesulfonate and camphorsulfonate), amino acid salts (e.g., aspartate and glutamate), quaternized amine salts, alkali metal salts (e.g., sodium salt and potassium salt), alkaline earth metal salts (e.g., magnesium salt and calcium salt), organic amine salts (e.g., salts formed with organic base such as trimethylamine, triethylamine, pyridine, picoline, dicyclohexylamine, N,N'-dibenzylethylenediamine, arginine and lysine) and ammonium salts. Above all, hydrochloride is particularly preferable. An orexin receptor antagonist or a salt thereof may exist in a form of solvate according to its types. According to the present invention, such solvates are included in the orexin receptor antagonists or the salts thereof. A solvate may be either a hydrate or a non-hydrate, preferably a hydrate. Non-hydrates may be, for example, alcohols (e.g., methanol, ethanol and n-propanol) and dimethylformamide.

In an anxiolytic drug of the invention, the proportion of an orexin receptor antagonist, a salt thereof or a solvate thereof as an active ingredient may appropriately be determined without limitation, including, for example, 0.01% or more by weight, more preferably 1% or more by weight, yet more preferably 10% or more by weight to a whole anxiolytic drug. A sufficient anxiolytic action can be obtained by meeting the proportion of the active ingredient in the above ranges.

Preferably, an orexin receptor antagonist, a salt thereof or a solvate thereof as an active ingredient is purified to a higher purity, including but not limited to a purity of preferably 50% or higher, more preferably 80% or higher and more preferably 90% or higher.

The anxiolytic drugs of the invention can be administered to a human or a non-human mammal via various administration routes, specifically, oral or parenteral routes (e.g., intravenous injection, intramuscular injection, subcutaneous administration, rectal administration and transdermal administration). Therefore, a compound used with the present invention (i.e., an orexin receptor antagonist, a salt thereof or a solvate thereof) may be used alone or formulated into an appropriate formulation using a pharmaceutically acceptable carrier according to a conventional method depending on the administration route.

Examples of preferable formulations include, as oral agents, a tablet, powder, subtle granule, granule, a coated tablet, a capsule, syrup and lozenge, and, as parenteral agents, an inhaler, a suppository, an injection solution (including infusion), an ointment, eye-drops, an eye ointment, nasal drops, ear drops, a skin patch, lotion and liposome.

Examples of carriers used for preparing these formulations include, for example, generally used excipients, binders, disintegrating agents, lubricants, colorants and flavoring agent, as well as, if necessary, stabilizers, emulsifiers, absorption promoters, surfactants, pH regulators, antiseptic agents, antioxidants, fillers, wetting agents, surface active agents, dispersants, buffers, preservatives, solubilizing agents and soothing agents. These can be formulated according to a conventional procedure by blending known components that can be used as materials for preparing a pharmaceutical preparation.

Such components that are usable and nontoxic include, for example, animal and vegetable oils such as soybean oil, beef fat and synthetic glyceride; hydrocarbons such as liquid paraffin, squalane oil and solid paraffin; ester oils such as octyldodecyl myristate and isopropyl myristate; higher alcohols such as cetostearyl alcohol and behenyl alcohol; silicon resin; silicon oil; surfactants such as polyoxyethylene fatty acid ester, sorbitan fatty acid ester, glycerine fatty acid ester, polyoxyethylene sorbitan fatty acid ester, polyoxyethylene hydrogenated castor oil and polyoxyethylene-polyoxypropylene block copolymers; water-soluble polymers such as hydroxyethylcellulose, polyacrylic acid, carboxy vinyl polymer, polyethyleneglycol, polyvinylpyrrolidone and methylcellulose; lower alcohols such as ethanol and isopropanol; polyalcohols (polyols) such as glycerine, propylene glycol, dipropylene glycol, sorbitol and polyethyleneglycol; sugars such as glucose and sucrose; inorganic powder such as silicic acid anhydride, magnesium aluminum silicate and aluminum silicate; inorganic salts such as sodium chloride and sodium phosphate; purified water; and their salts or their solvates.

Examples of excipients preferably include lactose, fructose, cornstarch, white sugar, glucose, mannitol, sorbit, crystalline cellulose and silicon dioxide. Examples of binders preferably include polyvinyl alcohol, polyvinyl ether, methylcellulose, ethylcellulose, gum arabic, tragacanth, gelatin, shellac, hydroxypropyl methylcellulose, hydroxypropyl cellulose, polyvinylpyrrolidone, polypropylene glycol polyoxyethylene block copolymer and meglumine. Examples of disintegrating agents preferably include starch, agar, gelatin powder, crystalline cellulose, calcium carbonate, sodium hydrogencarbonate, calcium citrate, dextrin, pectin and carboxymethylcellulose calcium. Examples of lubricants preferably include magnesium stearate, talc, polyethyleneglycol, silica and hydrogenated vegetable oil. Examples of colorants preferably include those that are allowed as additives in agents. Examples of flavoring agents preferably include cocoa powder, menthol, aromatic powder, mint oil, borneol and cinnamon powder. All of the components above may comprise their salts and solvates.

For example, in the case of oral formulation, an excipient and, if necessary, a binder, a disintegrating agent, a lubricant, a colorant and a flavoring agent or the like are added to a compound used in the present invention (an orexin receptor antagonist, a salt thereof or a solvate thereof), which is then formulated into, for example, powder, subtle granule, granule, a tablet, a coated table, a capsule or the like according to a conventional technique. In the case of tablets and granules, sugarcoating or other coating may be provided by a known procedure. In the case of syrup, injection formulation or the like, for example, a pH regulator, a solubilizer and a tonicity agent, and, if necessary, a solubilizing agent, a stabilizer and the like may be added for formulation by a conventional technique. A topical agent may be produced by any conventional technique without being limited to a particular formulation technique. As the base materials, various materials that are conventionally used for medicines, medicated cosmetics, cosmetics and the like can be used, including, for example, animal and vegetable oils, mineral oils, ester oil, wax, higher alcohols, fatty acids, silicon oil, surfactants, phospholipids, alcohols, polyalcohols, water-soluble polymers, clay minerals and purified water, and, if necessary, a pH regulator, an antioxidant, a chelating agent, an antiseptic/dust-resistant agent, a colorants, a flavoring agent and the like may be added. If needed, components such as a bloodstream promoter, a disinfectant, an antiphlogistic, a cellular stimulant, vitamins, amino acids, a moisturizer, a keratolytic agent and the like may be blended additionally. In this case, the proportion of the active ingredient to the carrier varies, without limitation, from 1 to 90% by weight.

When an anxiolytic drug of the invention is administered parenterally (e.g., administered by injection), the effective amount thereof varies depending on, for example, the degree of the condition, age, sex, weight, the administration route, the type of salt and the specific type of the disease. For example and without limitation, 30 µg to 1,000 mg, preferably 100 µg to 500 mg, more preferably 100 µg to 30 mg, more preferably 1 to 30 mg of the anxiolytic drug may be given daily in a single dose or in multiple doses to an adult weighing 60 kg.

When an anxiolytic drug of the invention is administered orally, the administration route and the effective amount thereof depend on the selection of the type of the compound used as an active ingredient (an orexin receptor antagonist, a salt thereof or a solvate thereof), the administered subject, the administration route, the property of the formulation, condition of the patient and physician's discretion. For example and without limitation, 30 µg to 10,000 mg, preferably 100 µg to 5,000 mg, more preferably 100 µg to 100 mg, more preferably 1 to 100 mg of the anxiolytic drug may be given daily in a single dose or in multiple doses to an adult weighing 60 kg.

In view that the efficiency varies according to the administration routes, a required dose is expected to vary widely. For example, an oral administration is expected to require higher dose than a parental administration such as intravenous injection. When administering to an infant, the dose may be lower than that administered to an adult. The administration method actually used may vary widely and may depart from the preferred administrations described herein. Such a variation in the dosage level may be appropriately controlled using a standard and empirical optimization procedure well known in the art.

The effect of the anxiolytic drugs of the invention on prevention and treatment of the diseases and conditions mentioned above may be confirmed by, for example and without limitation by Hamilton anxiety scale, clinical anxiety scale, self-rating anxiety scale and Sheehan anxiety scale.

The present invention also comprises use of an orexin receptor antagonist, a pharmacologically acceptable salt thereof or a solvate thereof for the production of an anxiolytic drug.

The present invention also comprises a method for treating and/or preventing anxiety, comprising administering an effective amount of an orexin receptor antagonist, a pharmacologically acceptable salt thereof or a solvate thereof to a patient.

3. Screening Method

A screening method of the invention (hereinafter, also referred to as "a method of the invention") is a method for selecting (screening) a compound having an anxiolytic action by using orexin-A as described above. Specifically, the method of the invention is based on a finding that the binding reactivity between orexin-A and an orexin receptor (orexin receptor-1, orexin receptor-2, especially the binding reactivity between orexin-A and orexin receptor-1, is very high, and a new finding that such binding by orexin-A raises anxiety action. The method of the invention uses orexin-A for screening a substance, particularly an orexin receptor antagonist, capable of inhibiting such binding in the presence of orexin-A (a substance having an antagonist action on orexin-A) among candidate substances (candidate compounds).

According to the present invention, candidate substances used for screening may be selected and assessed beforehand by known methods. By doing so, the method of the invention can be carried out more effectively and readily. For example, the "in vitro screening method" (e.g., binding assay, etc.) in the description above about "anxiolytic drugs" is preferably carried out beforehand to prepare more useful candidate substances.

Specifically, such methods of the invention preferably include, for example, the following two screening methods.

The first method for screening a compound having an anxiolytic action comprises: administering a candidate substance to a test animal and then inducing orexin-A secretion in the test animal, or inducing orexin-A secretion in a test animal and then or at the same time administering a candidate substance to the test animal; and analyzing the presence of anxiety in the test animal.

The second method for screening a compound having an anxiolytic action comprises: administering a candidate substance to a test animal and then administering orexin-A to the test animal, or administering orexin-A to a test animal and then or at the same time administering a candidate substance to the test animal; and analyzing the presence of anxiety in the test animal.

In these two methods, whether or not the administered candidate substance has an anxiolytic action can readily be assessed based on the obtained results of the analysis. Anxiety is raised in the test animal by utilizing the physiologically active action (anxiogenic action) of orexin-A. Preferably, orexin-A secretion is induced in the test animal or orexin-A is administered to the test animal as described above.

Hereinafter, types and steps of the screening methods of the invention will be illustrated.

(1) In the case where anxiety is raised by inducing orexin-A secretion.

Method 1

Method 1 comprises the following sequential steps 1a to 1c.

Step 1a: A candidate substance is administered to a test animal. Preferably, the candidate substance is administered intracerebroventricularlly.

Step 1b: According to the intended test (e.g., a light-dark exploration test or an elevated plus maze test (same applies to Methods 2 to 6); which will be described in detail below), a test animal is placed in an environment that raises anxiety. Thus, in this method, orexin-A secretion is induced in the test animal by an environmental change.

Step 1c: Based on the results of the test, the presence (degree) of anxiety in the test animal is analyzed and assessed, thereby determining whether the candidate substance has an anxiolytic action for selection.

Method 2

Method 2 comprises the following sequential steps 2a to 2c. Method 2 is similar to Method 1 except that step 1a is carried out after step 1b (i.e., the order of steps 1a and 1b is reversed).

Step 2a: According to the intended test method, a test animal is placed in an environment that raises anxiety. Thus, in this method, orexin-A secretion is induced in the test animal by an environmental change.

Step 2b: A candidate substance is administered to the test animal. Preferably, the candidate substance is administered intracerebroventricularlly.

Step 2c: Based on the results of the test, the presence (degree) of anxiety in the test animal is analyzed and assessed, thereby determining whether the candidate substance has an anxiolytic action for selection.

Method 3

Method 3 comprises the following sequential steps 3a and 3b. Method 3 is similar to Method 1 except that step 1a and step 1b are carried out simultaneously.

Step 3a: According to the intended test method, a test animal is placed in an environment that raises anxiety and at the same time administered with a candidate substance. Thus, in this method, orexin-A secretion is induced in the test animal by an environmental change simultaneously with administration of a candidate substance. Preferably, the candidate substance is administered intracerebroventricularlly. Thus, in Method 3, the candidate substance is administered simultaneously with orexin-A secretion. The phrase "administered simultaneously with" is not limited to a strict interpretation of administration at exactly the same time with in vivo orexin-A secretion, and the phrase applies to any substantially simultaneous case in medical and physiological viewpoints. For example, a candidate substance may automatically or manually be administered to an animal in a continuous or intermittent manner while orexin-A secretion is induced, in which case a little time difference between secretion and administration is accepted and considered substantially simultaneous, and an embodiment can be configured appropriately.

Step 3b: Based on the results of the test, the presence (degree) of anxiety in the test animal is analyzed and assessed, thereby determining whether the candidate substance has an anxiolytic action for selection.

(2) In the case where anxiety is raised by administering orexin-A.

Method 4

Method 4 comprises the following sequential steps 4a to 4d.

Step 4a: A candidate substance is administered to a test animal. Preferably, the candidate substance is administered intracerebroventricularlly.

Step 4b: Orexin-A is administered to the test animal. Preferably, orexin-A is administered intracerebroventricularlly.

Step 4c: According to the intended test method, the test animal is placed in an environment that raises anxiety.

Step 4d: Based on the results of the test, the presence (degree) of anxiety in the test animal is analyzed and assessed, thereby determining whether the candidate substance has an anxiolytic action for selection.

Method 5

Method 5 comprises the following sequential steps 5a to 5d. Method 5 is similar to Method 4 except that step 4a is carried out after step 4b (i.e., the order of steps 4a and 4b is reversed).

Step 5a: Orexin-A is administered to a test animal. Preferably, orexin-A is administered intracerebroventricularlly.

Step 5b: A candidate substance is administered to the test animal. Preferably, the candidate substance is administered intracerebroventricularlly.

Step 5c: According to the intended test method, the test animal is placed in an environment that raises anxiety.

Step 5d: Based on the results of the test, the presence (degree) of anxiety in the test animal is analyzed and assessed, thereby determining whether the candidate substance has an anxiolytic action for selection.

Method 6

Method 6 comprises the following sequential steps 6a to 6c. Method 6 is similar to Method 4 except that step 4a and step 4b are carried out simultaneously.

Step 6a: A candidate substance and orexin-A are simultaneously administered to a test animal. Preferably, the candidate substance and orexin-A are administered intracerebroventricularlly. Simultaneous administration of the candidate substance and orexin-A is not limited to a strict interpretation that they are mixed together and administered at exactly the same time, and the phrase applies as long as they are administered substantially simultaneously in medical and physiological viewpoints. For example, a little time difference between the candidate substance and orexin-A administrations and difference in administration routes may be accepted and considered substantially simultaneous, and an administration embodiment can be configured appropriately.

Step 6b: According to the intended test method, a test animal is placed in an environment that raises anxiety.

Step 6c: Based on the results of the test, the presence (degree) of anxiety in the test animal is analyzed and assessed, thereby determining whether the candidate substance has an anxiolytic action for selection.

Methods 4, 5 and 6 in case (2) are similar to Methods 1, 2 and 3 in case (1), respectively, except that they comprise the step of intentionally administrating orexin-A to a test animal. Thus, according to Methods 4 to 6, unless conditions of other steps do not differ widely, the amount of orexin-A in a test animal will be higher than that in the cases of Methods 1 to 3. Therefore, a candidate substance with a higher anxiolytic action can be screened.

Examples of test animals that can be used in Methods 1 to 6 include mice, rats and guinea pigs. Mice and rats are preferable when a light-dark exploration test (as described hereinbelow) or an elevated plus maze test (as described hereinbelow) is carried out as the intended test method described above. The test animals are bred given free access to water and food under a light/dark cycle (for example, a cycle of 12 hours each of light and dark periods (for example, light period from 7:00 to 19:00, and dark period from 19:00 to 7:00)). The number of animals bred is, for example, about 2 to 10 mice per cage, preferably about 10 mice, and, for example, about 2 to 5 rats, preferably about 2 rats per cage.

A method for administrating a candidate substance to a test animal is not particularly limited and can suitably be configured. For example, in the case of intracerebroventricular administration, a conventional method for administrating a drug to a desired site can be employed without being limited thereto. For example, a test animal is first anesthetized, then subjected to an operation for placing a guide cannula to a desired site. After an appropriate healing period (for example, 7 to 14 days, preferably at least a week or so), an injection needle is inserted into the guide cannula through which a candidate substance is administered by using a microsyringe connected to a reflux pump. The amount of the candidate substance administered is not particularly limited and can be determined appropriately.

The candidate substance may be prepared as a solution at a predetermined concentration using an artificial cerebrospinal fluid. As the artificial cerebrospinal fluid, a conventionally-used known artificial cerebrospinal fluid can be used, preferably including but not limited to aCSF (glucose 10 mM, KCl 2 mM, NaCl 115 mM, $CaCl_2$ 2.5 mM, $MgSO_4$ 1.2 mM, $NaHCO_3$ 25 mM, $KH_2PO_4$ 2.2 mM; pH 7.4).

The method for administering orexin-A to the test animal may be the same as the method for administering the candidate substance. In the same manner as the candidate substance, orexin-A may also be prepared as a solution at a desired concentration by using an artificial cerebrospinal fluid.

The intended test method may be a known test method for placing the test animals in an environment that may raise anxiety, preferably including but not limited to a "light-dark exploration test" and an "elevated plus maze test". These two methods are described hereinbelow along with methods for analyzing and assessing the presence (degree) of anxiety in the test animals.

Light-dark Exploration Test

The light-dark exploration test may be conducted using a test apparatus including two compartments (a dark compartment and a light compartment). The dark compartment is surrounded by a black material such as plastic with a lid on top whereas the light compartment is surrounded by a white material such as plastic with an open top. The light and dark compartments are connected via a tunnel made of a black material such as plastic that allows access to both compartments.

The illumination of the test room is set appropriately (e.g., 10 to 1000 lux, preferably 150 lux). The test animals are habituated to a relatively dark illumination (e.g., lower than 50 lux, preferably 10 lux) in another room before (e.g., more than an hour before, preferably more than 3 hours before) the test starts (except upon administration). This test is conducted between a predetermined period of time (e.g., between 9:00 to 19:00, preferably between 13:00 to 16:00). When administration takes place before the test, it should be done, for example, within 180 minutes, preferably 15 to 30 minutes before the start of the test.

This test starts where the test animals are placed in the dark compartment. The test animals are allowed to move freely for a predetermined period of time after the test begins (e.g., for more than 5 minutes, preferably for 5 minutes) during which their behaviors are videotaped. In this test, 6 to 15, preferably 8 to 15 test animals per group (per test condition) are subjected to the same test.

At the end of the test, the total time spent in the light compartment is calculated for each test animal, and the results are expressed, for example, as "average time+SEM". Time spent by the test animal in the light compartment is defined as time where all limbs of the test animal stayed in the light compartment. The statistical analysis of the test results may be conducted by, for example, but without limitation, ANOVA (one-way analysis of variance) and subsequent Dunnett's test, or by Welch's t-test.

Since the test animals used in the test are habituated to a relatively dark illumination until just before the test, they should have a feeling of anxiety in the subsequent relatively light illumination zone. Therefore, in this light-dark exploration test, test animals that spent longer time in the light compartment can be assessed to have less anxiety, in other words, assessed to have their anxiety alleviated or eliminated.

In this test, the artificial cerebrospinal fluid used for preparation of the candidate substance solutions is used alone as a negative control. On the other hand, two or more concentrations can be prepared and tested for each of the candidate substances in artificial cerebrospinal fluid. In this case, if a candidate substance has an anxiolytic action, the dose (concentration) that shows effectiveness (significant difference) or tendency of dose (concentration) dependency can be analyzed and assessed.

Elevated Plus Maze Test

The elevated plus maze test can be carried out according to the test procedure described in S. Pellow et al. (J. Neurosci. Methods, vol. 14 (1985), p-149-167).

A cross-shaped test apparatus consisting of two open arms and two closed arms each connected collinearly to a common central platform is placed at a certain height (e.g., 30 to 100 cm, preferably 40 to 50 cm above the floor). The rims of the open arms (the edges along the width direction) are provided with raised lips at a certain height (e.g., 0.1 to 1.0 cm, preferably 0.3 to 0.5 cm) to prevent the test animals from easily falling. Preferably, all of the members of the test apparatus are made of plastic. Preferably, colors and transparency of the test apparatus are such that dark color (such as gray) is used for the floor and the lips while walls of the closed arms are clear and colorless.

The illumination in the test room is set appropriately (e.g., 5 to 200 lux, preferably 5 to 20 lux). The test animals are habituated to a relatively light illumination (e.g., 10 to 1000 lux, preferably 20 to 500 lux) in another room before (e.g., more than an hour before, preferably more than 3 hours before) the test starts (except upon administration). This test is conducted between a predetermined period of time (e.g., between 9:00 to 19:00, preferably between 13:00 to 16:00). When administration takes place before the test, it should be done, for example, within 180 minutes, preferably 15 to 30 minutes before the test.

This test starts where the test animal is placed at the end of the closed arm facing outside from the center of the test apparatus, or the test animal is placed in a clear box placed at the center of the apparatus which is removed after a predetermined time to start the test. The test animals are allowed to move freely for a predetermined period of time after the test begins (e.g., for more than 5 minutes, preferably 5 minutes) during which their behaviors are videotaped. In this test, 6 to 15, preferably 8 to 15 test animals per group (per test condition) are subjected to the same test.

At the end of the test, the total time spent in the open arms is calculated for each test animal, and the results are expressed, for example, as "average time+SEM". Time spent by the test animal in the open arms is defined as time where all limbs of the test animal stayed in the open arms. The statistical analysis of the test results may be conducted by, for example, but without limitation, ANOVA (one-way analysis of variance) and subsequent Dunnett's test, or by Welch's t-test.

Since the test animals used in this test are habituated to a relatively light illumination until just before the test, they should have a feeling of anxiety to stay in the open arms where there is no side walls under the subsequent relatively dark condition. Therefore, in this elevated plus maze test, test animals that spent longer time in the open arms are assessed to have less anxiety, in other words, assessed to have their anxiety alleviated or eliminated.

In this elevated plus maze test, the artificial cerebrospinal fluid used for preparation of the candidate substance solutions is used alone as a negative control. On the other hand, two or more concentrations can be prepared and tested for each of the candidate substances in artificial cerebrospinal fluid. In this case, if a candidate substance has an anxiolytic action, the dose (concentration) that shows effectiveness (significant difference) or tendency of dose (concentration) dependency can be analyzed and assessed.

Since compounds obtained by the screening method of the invention have anxiolytic actions, they can be used as active ingredients for anxiolytic drugs.

4. Screening Kit

In order to carry out the screening methods of the invention described above, a kit comprising orexin-A can be used for screening a compound having an anxiolytic action.

Preferably, orexin-A in the kit is cryopreserved, for example, as powder for the sake of stability (storage quality), and dissolved in an artificial cerebrospinal fluid described above on the day of experiment.

The kit may comprise components other than orexin-A. Other components include, for example, a guide cannula, dental cement (material for fixing the cannula), an injection needle, a microsyringe and a reflux pump.

The kit should at least comprise orexin-A as a component. Therefore, the kit may or may not comprise, along with orexin-A, all of the components necessary for screening a compound having an anxiolytic action. In the latter case, some or all of the necessary components other than orexin-A may be prepared at least by the time of carrying out the screening method.

EXAMPLES

Hereinafter, the present invention will be described specifically by way of examples. The present invention, however, is not limited to these examples.

Example 1

Confirmation of Anxiogenic Action of Orexin-A (1)

(1) Test Animals

C57BL/6NCrj mice (male, 25 to 30 g, Charles River, Japan) were used for the light-dark exploration test. Ten mice were bred per cage.

WISTAR rats (male, 300 to 400 g, Charles River, Japan) were used for the elevated plus maze test. Two mice were bred per cage.

These test animals were bred given free access to water and food under a cycle of 12 hours each of light and dark periods (light period from 7:00 to 19:00 and dark period from 19:00 to 7:00).

(2) Preparation of Orexin-A Solution

Orexin-A (Peptide Institute Inc., Osaka, Japan) was dissolved in an artificial cerebrospinal fluid (aCSF: glucose 10 mM, KCl 2 mM, NaCl 115 mM, $CaCl_2$ 2.5 mM, $MgSO_4$ 1.2 mM, $NaHCO_3$ 25 mM, $KH_2PO_4$ 2.2 mM; pH 7. 4) to prepare solutions at various concentrations (0.1 nmol/µl, 0.3 nmol/µl, 1.0 nmol/µl, 3.0 nmol/µl). The artificial cerebrospinal fluid was used alone as a negative control.

(3) Operation for Fixing Guide Cannula

Anesthesia of mice was performed before the operation using ketamine (100 mg/kg, i.p.) and xylazine (10 mg/kg, i.p.).

In the operation, a guide cannula for mouse (length 10 mm) was inserted such that the tip thereof was placed at a predetermined site of the lateral ventricle (i.e., 0.3 mm posterior (near the Lambda suture) and 0.9 mm right to the Bregma suture and 2.3 mm under the surface of the cortex), and fixed using Ketac™ Cem Maxicap™ dental cement (3M ESPE, Seefeld, Germany).

Anesthesia of rats was performed before the operation using ketamine (80 mg/kg, i.p.) and xylazine (8 mg/kg, i.p.).

In the operation, a guide cannula for rat (length 17 mm) was inserted such that the tip thereof was placed at a predetermined site of the lateral ventricle (i.e., 0.8 mm posterior (near the Lambda suture) and 1.4 mm right to the Bregma suture and 3.0 mm under the surface of the cortex), and fixed using dental cement (GC Co., Tokyo. Japan).

Both mice and rats were given at least a week of healing period was given following the operation and prior to the test.

(4) Intracerebroventricular Administration

A stainless-steel injection needle was used that can be inserted into the lateral ventricle to a point 0.5 mm deeper than the tip of the guide cannula for intracerebroventricularly administering an orexin-A solution. The amounts of orexin-A solution were 2 μl and 5 μl for mice and rats, respectively. A microsyringe (705N 50 μl, Hamilton, Nevada, USA) was connected to a reflux pump (CMA100, BAS Inc., Tokyo, Japan) for injection at a precisely constant rate (1 μl/min for mice and 2.5 μl/min for rats).

The injection needle was left inserted into the guide cannula for a minute following administration so that an accurate amount was administered to the cerebral ventricle.

Ink (water pigment ink) was administered through the cannula after the test to confirm that the cannula was buried at the predetermined position.

(5) Behavioral Test and Statistical Analysis

As behavioral tests, mice and rats were subjected to a "light-dark exploration test" and an "elevated plus maze test", respectively, as follows.

Light-dark Exploration Test

The following four subject groups were tested.

aCSF (vehicle) administration group (aCSF, n=14)
0.1 nmol orexin-A administration group (OXA-0.1, n=15)
0.3 nmol orexin-A administration group (OXA-0.3, n=16)
1.0 nmol orexin-A administration group (OXA-1.0, n=17)

The test apparatus consisted of two compartments, namely a dark compartment (depth 10 cm×width 15 cm×length 20 cm) and a light compartment (depth 20 cm×width 15 cm×length 20 cm). Specifically, the dark compartment was made using a black plastic material with a lid on top whereas the light compartment was made using a white plastic material with an open top. Both of the light and dark compartments were connected via a black plastic tunnel (depth 7 cm×width 10 cm×length 4.5 cm) that allows access to both compartments.

The illumination of the test room was set to 150 lux. The test animals were habituated to an illumination of 10 lux in another room for more than 3 hours before starting the test (except upon administration). This test was conducted between 13:00 to 16:00.

For all of the test subjects, intracerebroventricular administrations to the test animals took place 15 minutes before the test.

The test started where the test animals were placed in the dark compartment. The test animals were allowed to move freely for the first 5 minutes of the test during which their behaviors were videotaped. In this test, 14, 15, 16 and 17 mice from the aCSF administration group, the 0.1 nmol orexin-A administration group, the 0.3 nmol orexin-A administration group and the 1.0 nmol orexin-A administration group, respectively, were individually subjected to the same test.

At the end of the test, the total time spent in the light compartment was calculated for each test animal, and the results were expressed as "average time+SEM" (see FIG. 1). As described above, time spent by the test animal in the light compartment was defined as time where all limbs of the test animal stayed in the light compartment. The statistical analysis of the results from the test was conducted by ANOVA (one-way analysis of variance) and subsequent Dunnett's test.

Elevated Plus Maze Test

The following five subject groups were tested.

aCSF (vehicle) administration group (aCSF, n=6)
0.1 nmol orexin-A administration group (ORX-0.1, n=5)
0.3 nmol orexin-A administration group (ORX-0.3, n=5)
1.0 nmol orexin-A administration group (ORX-1.0, n=6)
3.0 nmol orexin-A administration group (ORX-3.0, n=5)

The elevated plus maze test was basically carried out according to the test procedure described in S. Pellow et al. (J. Neurosci. Methods, vol. 14 (1985), p-149-167).

A cross-shaped test apparatus consisted of two open arms (width 10 cm×length 50 cm) and two closed arms (width 10 cm×length 50 cm, with 40 cm-high walls provided widthwise along the edges) each connected collinearly to a common central platform (depth 10 cm×width 10 cm), which was placed at about 50 cm above the floor. The rims of the open arms (the edges in width direction) were provided with raised lips 0.5 cm high to prevent the test animals from easily falling. All members of the test apparatus were made of plastic, with gray floor and clear and colorless walls for the closed arms.

The illumination in the test room was set to 8 lux. The test animals were habituated to an illumination of 500 lux in another room for more than 3 hours before starting the test (except upon administration). This test was conducted between 13:00 to 16:00.

For all of the test subjects, administration took place 15 minutes before the test.

This test started where the test animal was placed at the end of the closed arm facing outside from the center of the test apparatus. The test animals were allowed to move freely for the first 5 minutes during which their behaviors were videotaped. In this test, 6, 5, 5, 6 and 5 rats from the aCSF administration group, the 0.1 nmol orexin-A administration group, the 0.3 nmol orexin-A administration group, the 1.0 nmol orexin-A administration group and the 3.0 nmol orexin-A administration group, respectively, were individually subjected to the same test.

Figure 2:
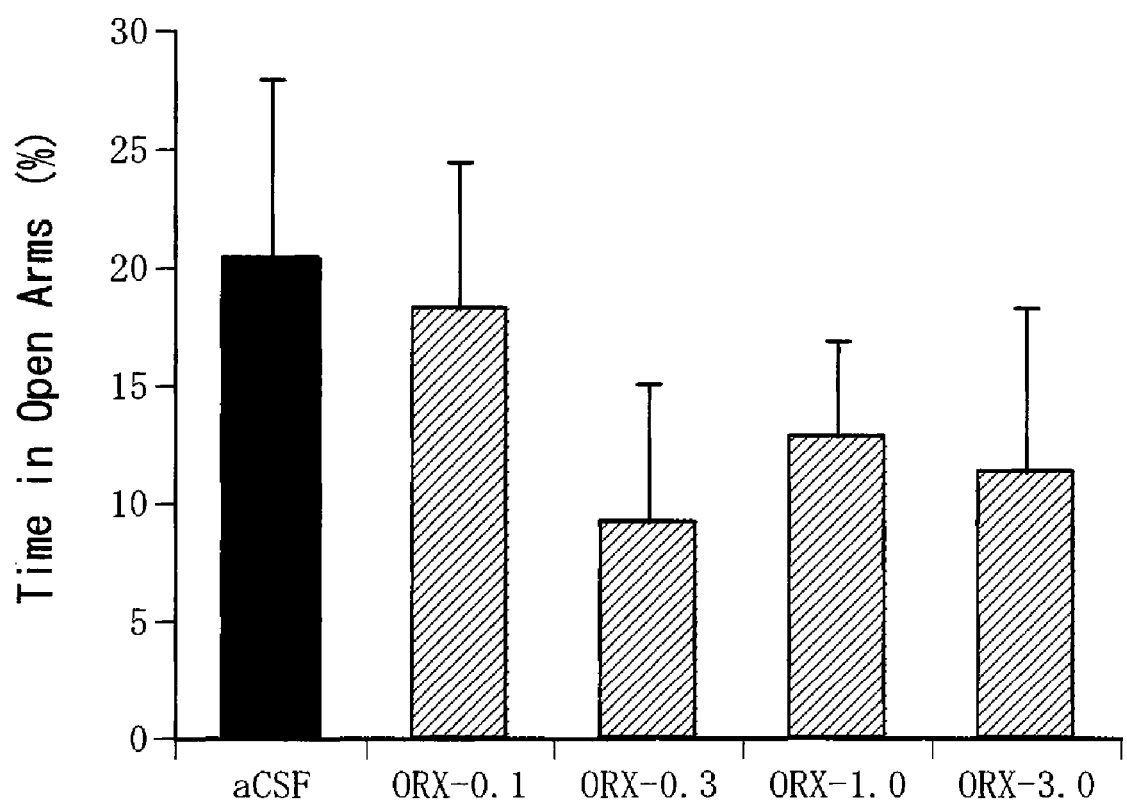
FIG. 2 shows the results from the elevated plus maze test conducted in Example 1 for confirming the anxiogenic action of orexin-A.

At the end of the test, the total time spent in the open arms was calculated for each test animal, and the results were expressed as "average time+SEM" for each test subject (see FIG. 2). As described above, time spent by the test animal in the open arms was defined as time where all limbs of the test animal stayed in the open arms. The statistical analysis of the test results was conducted by ANOVA (one-way analysis of variance) and subsequent Dunnett's test.

(6) Assessment Results

From the following assessment results, orexin-A was confirmed to have an anxiogenic action.

Specifically, intracerebroventricular administration of the orexin-A solution to mice significantly shortened the time spent in the light compartment (see FIG. 1). In particular, the 0.1 nmol orexin-A administration group and the 1.0 nmol orexin-A administration group showed significant difference from the aCSF administration group (*$p<0.05$, t-test; **$p<0.01$, t-test).

Similarly, intracerebroventricular administration of orexin-A solution to rats shortened time spent in the open arms (see FIG. 2). Time spent on the open arms shortened volume-dependently.

Example 2

Confirmation of Anxiogenic Action of Orexin-A (2)

(1) Test Animals

C57BL/6NCrj mice (male, 25 to 30 g, Charles River, Japan) were used. Ten mice were bred per cage.

These test animals were bred given free access to water and food under a cycle of 12 hours each of light and dark periods (light period from 7:00 to 19:00 and dark period from 19:00 to 7:00).

(2) Preparation of Orexin-A Solution

Orexin-A (Peptide Institute Inc., Osaka, Japan) was dissolved in an artificial cerebrospinal fluid (aCSF: glucose 10 mM, KCl 2 mM, NaCl 115 mM, $CaCl_2$ 2.5 mM, $MgSO_4$ 1.2 mM, $NaHCO_3$ 25 mM, $KH_2PO_4$ 2.2 mM; pH 7.4) to prepare a solution at a predetermined concentration (1.0 nmol/μl). The artificial cerebrospinal fluid was used alone as a negative control.

(3) Operation for Fixing Guide Cannula

Anesthesia of mice was performed before the operation using ketamine (100 mg/kg, i.p.) and xylazine (10 mg/kg, i.p.).

In the operation, a guide cannula for mouse (length 10 mm) was inserted such that the tip thereof was placed at a predetermined site of the lateral ventricle (i.e., 0.3 mm posterior (near the Lambda suture) and 0.9 mm right to the Bregma suture and 2.3 mm under the surface of the cortex), and fixed using Ketac™ Cem Maxicap™ dental cement (3M ESPE, Seefeld, Germany).

Test animals were given at least a week of healing period following the operation and prior to the test.

(4) Intracerebroventricular Administration

A stainless-steel injection needle was used that can be inserted into the lateral ventricle at a point 0.5 mm deeper than the tip of the guide cannula for intracerebroventricular administration of the orexin-A solution. The amount of the orexin-A solution was 2 μl. A microsyringe (705N 50 μl, Hamilton, Nevada, USA) was connected to a reflux pump (CMA100, BAS Inc., Tokyo, Japan) for injection at a precisely constant rate (1 μl/min).

The injection needle was left inserted into the guide cannula for a minute following administration so that an accurate amount was administered in the cerebral ventricle.

Ink (water pigment ink) was administered through the cannula after the test to confirm that the cannula was buried at the predetermined position.

(5) Behavioral Test and Statistical Analysis

As a behavioral test, an "elevated plus maze test" was carried out by following the procedure below.

Elevated Plus Maze Test

The following two subject groups were tested.

aCSF (vehicle) administration group (aCSF, n=8)

1.0 nmol orexin-A administration group (ORX-1.0, n=9)

The elevated plus maze test was basically carried out according to the test procedure described in S. Pellow et al. (J. Neurosci. Methods, vol. 14 (1985), p-149-167).

A cross-shaped test apparatus consisted of two open arms (width 5 cm×length 30 cm) and two closed arms (width 5 cm×length 30 cm, with 15 cm-high walls provided widthwise along the edges) each connected collinearly to a common central platform (depth 5 cm×width 5 cm), which was placed at about 45 cm above the floor. The rims of the open arms (the edges in width direction) were provided with raised lips 0.3 cm high to prevent the test animals from easily falling. All members of the test apparatus were made of plastic, with gray floor and gray walls for the closed arms.

The illumination in the test room was set to 10 lux. The test animals were habituated to an illumination of 20 lux in another room for more than 3 hours before starting the test (except upon administration). This test was conducted between 13:00 to 16:00.

For both test subjects, administration took place 15 minutes before the test.

The test animal was placed in a clear box (depth 7.8 cm×width 7.8 cm×height 18 cm) placed at the center of the test apparatus for a minute, which was then removed to start the test. The test animals were allowed to move freely for the first 5 minutes during which their behaviors were videotaped. In this test, 8 and 9 mice from the aCSF administration group and the 1.0 nmol orexin-A administration group, respectively, were individually subjected the same test.

Figure 3:
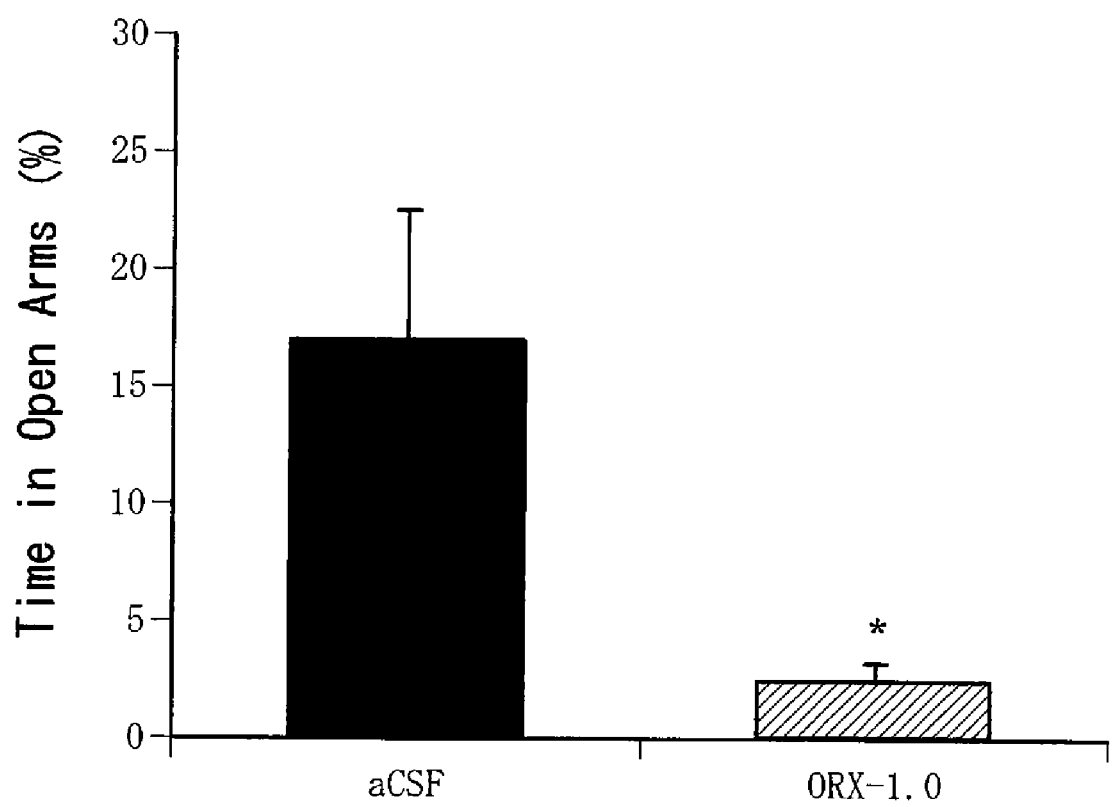
FIG. 3 shows the results from the elevated plus maze test conducted in Example 2 for confirming anxiogenic action of orexin-A.

At the end of the test, the total time spent in the open arms was calculated for each test animal, and the results were expressed as "average time+SEM" for each test subject (see FIG. 3). As described above, time spent by the test animal in the open arms was defined as time where all limbs of the test animal stayed in the open arms. The statistical analysis of the test results was conducted by Welch's t-test.

(6) Assessment Results

From the following assessment results, orexin-A was confirmed to have an anxiogenic action. Specifically, intracerebroventricular administration of the orexin-A solution to the animals significantly shortened time spent in the light compartment (see FIG. 3). Significant difference was seen between the two groups, i.e., the 1.0 nmol orexin-A administration group and the aCSF administration group (*p<0.05, t-test).

Example 3

Anxiolytic Drug Containing Orexin Receptor Antagonist

1. Synthesis of Orexin Receptor-1 Antagonist

A compound having a function as an orexin receptor-1 antagonist, (1-(2-methylbenzoxazole 6-yl)-3-[1,5]naphthyridine-4-yl urea (SB-334867) hydrochloride) was synthesized. Specifically, synthesis was carried out according to the following steps (1) to (3) following the procedure described in the method of Example 6 in WO 99/58533.

(1) Synthesis of 4-amino-1,5-naphthyridine (CAS No. 7689-63-6)

To 700 mg of 4-hydroxy-1,5-naphthyridine (CAS No. 5423-54-1, purchased from Specs), phosphorous oxychloride (15 ml) was added and heated to reflux for an hour. The reaction was put back to room temperature. The mixture was poured to ice, made alkaline with ammonia water and extracted with ethyl acetate. The ethyl acetate layer was washed with water, dried with magnesium sulfate, filtrated through NH silica gel, and the filtrate was concentrated under reduced pressure to obtain 456 mg of 4-chloro-1,5-naphthyridine (CAS No. 7689-63-6). To the obtained 4-chloro-1,5-naphthyridine (456 mg), pyridine (19 ml) and n-propylamine hydrochloride (1.32 g) were added and heated to reflux for 3.5 hours. The mixture was cooled to room temperature, concentrated under reduced pressure, and the obtained residue was partitioned between diethyl ether and 2N aqueous sodium hydroxide. The ether layer was separated and dried with magnesium sulfate. Solvent was distilled away and the residue was purified with NH silica gel (ethyl acetate/heptane system) to obtain 345 mg of the title compound (CAS No. 7689-63-6). The same operation was repeated to synthesize for another 952 mg. The structure of the obtained title compound and results from NMR measurement were as follows.

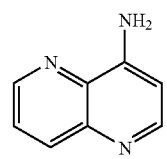

$^1$H NMR (CDCl$_3$) δ (ppm): 5.54 (2H, brs), 6.74 (1H, d, J=5 Hz), 7.58 (1H, dd, J=4+8 Hz), 8.25 (1H, dd, J=2+8 Hz), 8.53 (1H, d, J=5 Hz), 8.75 (1H, dd, J=2+4 Hz).

(2) Synthesis of 2-methyl-6-benzoxazole Carboxylic Acid (CAS No. 13452-14-7)

11.0 g of methyl 4-amino-3-hydroxybenzoate (CAS No. 63435-16-5, purchased from Lancaster) was dissolved in xylene (220 ml)-tetrahydrofuran (110 ml) at room temperature. To this solution, acetyl chloride (4.73 ml) was added and heated to reflux for 6 hours. The mixture was partitioned between 1N aqueous hydrochloric acid and ethyl acetate and the ethyl acetate layer was separated. The ethyl acetate layer was washed with saturated aqueous sodium chloride, and then dried with magnesium sulfate. The mixture was filtrated, and the filtrate was concentrated under reduced pressure. The obtained residue was passed through a silica gel flash chromato (ethyl acetate/heptane system) to obtain 10 g of methyl 4-acetamide-3-hydroxybenzoate crude product. To the crude product, acetic acid (250 ml) was added and heated to reflux for 6 hours, and the mixture was concentrated under reduced pressure. The residue was partitioned between ethyl acetate and saturated aqueous sodium hydrogen carbonate, and the ethyl acetate layer was separated. The ethyl acetate layer was dried with magnesium sulfate, filtrated through NH silica gel, and the filtrate was concentrated under reduced pressure to obtain 9.52 g of 2-methyl-6-benzoxazole carboxylic acid methyl ester. To the obtained 2-methyl-6-benzoxazole carboxylic acid methyl ester (9.52 g), ethanol (100 ml) and 2N aqueous sodium hydroxide (49.8 ml) were added and stirred at 60° C. for 30 minutes. The mixture was concentrated under reduced pressure and acidified with 5N aqueous hydrochloric acid. The precipitate was filtrated, washed with water, dried and then recrystallized with ethanol to obtain 4.62 g of the title compound (CAS No. 13452-14-7). The structure of the obtained title compound and results from NMR measurement were as follows.

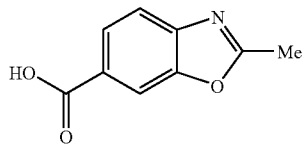

$^1$H NMR (CD$_3$OD) δ (ppm): 2.67 (3H, s), 7.67 (1H, d, J=8 Hz), 8.05 (1H, dd, J=1+8 Hz), 8.19 (1H, d, J=1 Hz).

(3) Synthesis of 1-(2-methylbenzoxazole-6-yl)-3-[1,5]naphthyridine-4-yl urea hydrochloride (CAS No. 249889-64-3)

To 2-methyl-6-benzoxazole carboxylic acid (1.060 g) in toluene (111 ml) solution, triethylamine (0.867 ml) and N,N-dimethylformamide (22 ml) were added. To this mixture, diphenyl phosphoryl azide (1.65 ml) was added and stirred at 65° C. for an hour. The reaction mixture was cooled to room temperature, added with 4-amino-1,5-naphthyridine (0.878 g), and the resulting mixture was stirred at 65° C. for another 72 hours. The cooled mixture was diluted with ethyl acetate and washed with a saturated aqueous sodium carbonate. The organic layer was dried with magnesium sulfate and the solvent was distilled away to obtain a crude product of 1-(2-methylbenzoxazole-6-yl)-3-[1,5]naphthyridine-4-yl urea for 0.797 g. The crude product was dissolved in ethyl acetate at 60° C., added with 4N-hydrogen chloride-ethyl acetate solution and stirred on ice. The precipitated hydrochloride was filtrated, air-dried at 60° C. to obtain 840 mg of the title compound (CAS No. 249889-64-3). The structure of the obtained title compound and results from NMR measurement were as follows.

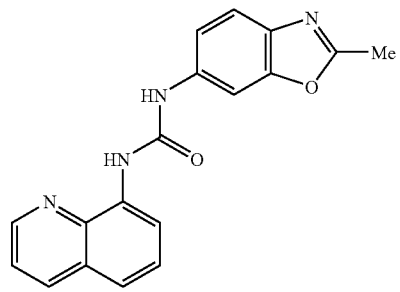

$^1$H NMR (DMSO-d$_6$) δ (ppm): 2.61 (3H, s), 7.30 (1H, dd, J=2+9 Hz), 8.08 (1H, d, J=2 Hz), 8.13 (1H, dd, J=4+9 Hz), 8.62 (1H, dd, J=1+9 Hz), 8.73 (1H, d, J=6 Hz), 9.09 (1H, d, J=6 Hz), 9.19 (1H, dd, 1+4 Hz), 10.71 (1H, s), 10.79 (1H, s). MS(ESI): 320 (MH$^+$), 342 (MNa$^+$).

2. Confirmation of Anxiolytic Action (1) Test Animals

C57BL/6NCrj mice (male, 25 to 30 g, Charles River, Japan) were used. Ten mice were bred per cage.

These test animals were bred given free access to water and food under a cycle of 12 hours each of light and dark periods (light period from 7:00 to 19:00 and dark period from 19:00 to 7:00).

(2) Preparation of Candidate Substance

SB-334867 that was synthesized was dissolved in an artificial cerebrospinal fluid (aCSF: glucose 10 mM, KCl 2 mM, NaCl 115 mM, CaCl$_2$ 2.5 MM, MgSO$_4$ 1.2 mM, NaHCO$_3$ 25 mM, KH$_2$PO$_4$ 2.2 mM; pH 7.4) to prepare a solution at a predetermined concentration as a candidate substance.

Specifically, two types of solutions, 0.50 nmol/μl and 1.50 nmol/μl, were prepared. The artificial cerebrospinal fluid (aCSF) was used alone as a negative control.

(3) Operation for Fixing Guide Cannula

An operation was conducted for a fixing guide cannula as described in Example 1(3). A healing period was also given in the same manner.

(4) Intracerebroventricular Administration

An intracerebroventricular administration of the SB-334867 solution was performed as described in Example 1(4). The position of the inserted cannula was also confirmed in the same manner.

(5) Behavioral Test and Statistical Analysis

As behavioral tests, a "light-dark exploration test" was conducted according to the following procedure.

Light-dark Exploration Test

The following three subject groups were tested.

aCSF (vehicle) administration group (VEH, n=10)

1 nmol SB-334867 administration group (SB-1n, n=10)

3 nmol SB-334867 administration group (SB-3n, n=10)

The test apparatus consisted of a dark compartment (depth 10 cm×width 15 cm length 20 cm) and a light compartment (depth 20 cm×width 15 cm×length 20 cm). Specifically, the dark compartment was made of a black plastic material with a lid on top whereas the light compartment was made of a white plastic material with an open top. Both of the light and dark compartments were connected via a black plastic tunnel (depth 7 cm×width 10 cm×length 4.5 cm) that allows access to both compartments.

The illumination of the test room was set to 150 lux. The test animals were habituated to an illumination of 10 lux in another room for more than 3 hours before starting the test (except upon administration). This test was conducted between 13:00 to 16:00.

For all of the test subjects, intracerebroventricular administrations took place 15 minutes before the test.

The test started where the test animals were placed in the dark compartment. The test animals were allowed to move freely for the first 5 minutes during which their behaviors were videotaped. In this test, 10 mice from each of the aCSF administration group, the 1 nmol SB-334867 administration group and the 3 nmol SB-334867 administration group were individually subjected to the same test.

Figure 4:
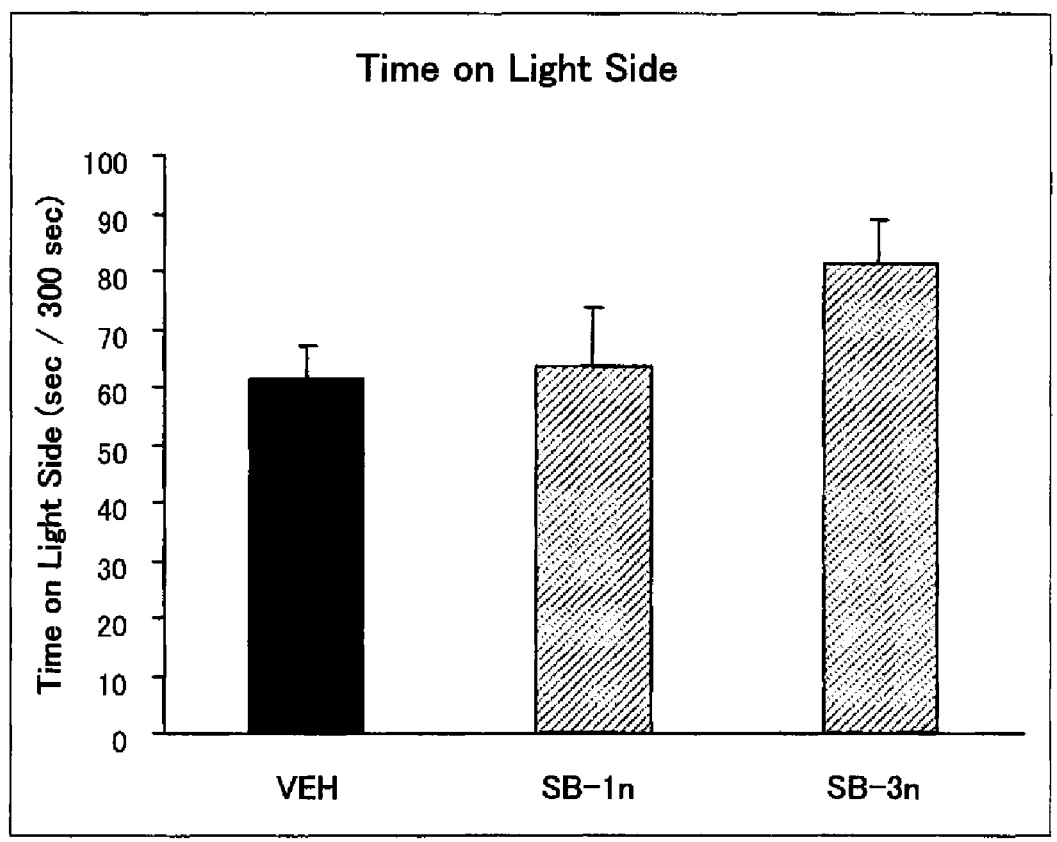
FIG. 4 shows the results from the light-dark exploration test conducted in Example 3 for screening a compound with an anxiolytic action where a SB-334867 solution is used as a candidate substance.

At the end of the test, the total time spent in the light compartment was calculated for each test animal, and the results were expressed as "average time+SEM" for each test subject (see FIG. 4). As described above, time spent by the test animal in the light compartment was defined as time where all limbs of the test animal stayed in the light compartment. The statistical analysis of the results from the test was conducted by ANOVA (one-way analysis of variance) and subsequent Dunnett's test.

(6) Assessment Results

From the following assessment results, SB-334867 (a solution containing SB-334867) was confirmed to have an anxiogenic action and thus found to be useful as an anxiolytic drug. Specifically, intracerebroventricular administration of SB-334867 lengthened time spent in the light compartment dosage-dependently (see FIG. 4).

What is claimed is:

1. A method for identifying a compound having anxiolytic action, which method comprises:
    (a) administering a candidate compound to a test animal in combination with orexin-A; and
    (b) determining whether anxieties of the test animal are ameliorated compared to anxieties of a control animal not administered the candidate compound,
    wherein the candidate compound is identified as a compound having an anxiolytic action when anxieties of the test animal are ameliorated compared to anxieties of the control animal.

2. The method according to claim 1, wherein orexin-A is administered to the test animal concurrently with administration of the candidate compound.

3. The method according to claim 1, wherein orexin-A is administered to the test animal prior to administration of the candidate compound.

4. The method according to claim 1, wherein orexin-A is administered to the test animal after administration of the candidate compound.

* * * * *